US012376868B2

(12) United States Patent
Gogarty et al.

(10) Patent No.: US 12,376,868 B2
(45) Date of Patent: Aug. 5, 2025

(54) DEVICES AND METHODS FOR POSTERIOR RESECTION IN ROBOTICALLY ASSISTED PARTIAL KNEE ARTHROPLASTIES

(71) Applicant: Orthosoft ULC, Montreal (CA)

(72) Inventors: Emily Gogarty, Montreal (CA); Jean-Sebastien Merette, Mont-St-Hiliare (CA); Benoit Pelletier, Laval (CA); Suntara Ly, Longueuil (CA); Emmanuelle Bouvier, Val-David (CA); Adam H. Sanford, Minneapolis, MN (US); Jess H. Lonner, Philadelphia, PA (US)

(73) Assignee: Orthosoft ULC

(*) Notice: Subject to any disclaimer, the term of this patent is extended or adjusted under 35 U.S.C. 154(b) by 325 days.

(21) Appl. No.: 18/123,848

(22) Filed: Mar. 20, 2023

(65) Prior Publication Data

US 2023/0225747 A1 Jul. 20, 2023

Related U.S. Application Data

(63) Continuation-in-part of application No. 17/230,203, filed on Apr. 14, 2021, now Pat. No. 12,167,860.
(Continued)

(51) Int. Cl.
*A61B 34/20* (2016.01)
*A61B 17/17* (2006.01)
(Continued)

(52) U.S. Cl.
CPC ...... *A61B 17/1764* (2013.01); *A61B 17/1721* (2013.01); *A61B 34/20* (2016.02);
(Continued)

(58) Field of Classification Search
CPC .................. A61B 34/20–2034/306
See application file for complete search history.

(56) References Cited

U.S. PATENT DOCUMENTS

| 5,683,397 A | 11/1997 | Vendrely et al. |
| 7,686,812 B2 | 3/2010 | Axelson, Jr. et al. |

(Continued)

FOREIGN PATENT DOCUMENTS

| CA | 3114820 C | 10/2023 |
| CN | 110711029 A | 1/2020 |

(Continued)

OTHER PUBLICATIONS

"U.S. Appl. No. 17/230,203, Advisory Action mailed Apr. 5, 2024", 2 pgs.

(Continued)

*Primary Examiner* — Zade Coley
(74) *Attorney, Agent, or Firm* — SCHWEGMAN LUNDBERG & WOESSNER, P.A.

(57) ABSTRACT

A method of positioning posterior resection guides in a three-dimensional coordinate system using robotic arms to perform partial knee arthroplasties comprises connecting a first tracking device for a surgical tracking system of the robotic arm to a femur, connecting a second tracking device for the surgical tracking system of the robotic arm to a tibia, manually positioning the tibia relative to the femur to a desired orientation to perform a posterior resection, manually determining a position for the posterior resection guide to perform the posterior resection, digitizing a reference point for the posterior resection guide in the three-dimensional coordinate system for a location of a feature of the posterior resection guide, moving the posterior resection guide to the location in the three-dimensional coordinate system with the robotic arm, and resecting a posterior (Continued)

portion of a condyle of the femur using the posterior resection guide to guide a cutting instrument.

24 Claims, 17 Drawing Sheets

Related U.S. Application Data

(60) Provisional application No. 63/435,733, filed on Dec. 28, 2022, provisional application No. 63/010,761, filed on Apr. 16, 2020.

(51) Int. Cl.
| | | |
|---|---|---|
| *A61B 34/30* | (2016.01) | |
| *A61B 90/00* | (2016.01) | |
| *A61B 90/50* | (2016.01) | |
| *A61B 17/16* | (2006.01) | |
| *A61B 17/56* | (2006.01) | |

(52) U.S. Cl.
CPC .............. *A61B 34/30* (2016.02); *A61B 90/37* (2016.02); *A61B 90/50* (2016.02); *A61B 17/1675* (2013.01); *A61B 2017/564* (2013.01)

(56) References Cited

U.S. PATENT DOCUMENTS

| | | | |
|---|---|---|---|
| 8,884,618 B2 | 11/2014 | Mahfouz | |
| 9,675,461 B2 | 6/2017 | Mahfouz | |
| 10,136,952 B2 | 11/2018 | Couture et al. | |
| 2004/0260301 A1 | 12/2004 | Lionberger et al. | |
| 2007/0156157 A1 | 7/2007 | Nahum et al. | |
| 2007/0213738 A1 | 9/2007 | Martin et al. | |
| 2007/0270685 A1* | 11/2007 | Kang ................... | A61B 90/03 |
| | | | 600/424 |
| 2008/0177261 A1 | 7/2008 | Mcminn | |
| 2010/0036383 A1 | 2/2010 | Major et al. | |
| 2010/0160919 A1 | 6/2010 | Axelson, Jr. et al. | |
| 2010/0241126 A1 | 9/2010 | Ghijselings | |
| 2011/0046685 A1 | 2/2011 | Faure et al. | |
| 2013/0144302 A1 | 6/2013 | Reeve | |
| 2017/0042558 A1 | 2/2017 | Ghijselings | |
| 2017/0056022 A1 | 3/2017 | Cheal et al. | |
| 2017/0100132 A1 | 4/2017 | Collazo | |
| 2017/0290597 A1 | 10/2017 | Goble et al. | |
| 2017/0312035 A1* | 11/2017 | May ...................... | A61B 50/33 |
| 2018/0116739 A1* | 5/2018 | Gogarty ................ | B25J 9/1689 |
| 2018/0116740 A1 | 5/2018 | Gogarty et al. | |
| 2019/0240045 A1 | 8/2019 | Couture | |
| 2021/0093327 A1 | 4/2021 | Sun et al. | |
| 2021/0267611 A1* | 9/2021 | Hart ....................... | A61B 17/15 |
| 2021/0322032 A1* | 10/2021 | Gogarty ................ | A61B 34/20 |
| 2021/0353311 A1* | 11/2021 | Lavallee ................ | A61B 34/20 |
| 2021/0353367 A1* | 11/2021 | Krebs ................... | A61B 90/361 |
| 2022/0071769 A1* | 3/2022 | Farley ................... | A61B 34/30 |
| 2022/0183701 A1 | 6/2022 | Gogarty et al. | |
| 2022/0398744 A1* | 12/2022 | Couture ................ | A61B 34/20 |

FOREIGN PATENT DOCUMENTS

| | | |
|---|---|---|
| CN | 113520511 A | 10/2021 |
| EP | 3895649 A3 | 1/2022 |
| WO | WO-2015131138 A1 | 9/2015 |
| WO | WO-2018103945 A1 | 6/2018 |

OTHER PUBLICATIONS

"U.S. Appl. No. 17/230,203, Final Office Action mailed Feb. 20, 2024", 10 pgs.

"U.S. Appl. No. 17/230,203, Non Final Office Action mailed Jan. 4, 2024", 9 pgs.

"U.S. Appl. No. 17/230,203, Response filed Feb. 7, 2024 to Non Final Office Action mailed Jan. 4, 2024", 15 pgs.

"U.S. Appl. No. 17/230,203, Response filed Mar. 29, 2024 to Final Office Action mailed Feb. 20, 2024", 13 pgs.

"U.S. Appl. No. 17/230,203, Response filed Apr. 8, 2024 to Advisory Action mailed Apr. 5, 2024", 16 pgs.

"U.S. Appl. No. 17/230,203, Response filed Nov. 8, 2023 to Restriction Requirement mailed Sep. 8, 2023", 7 pgs.

"U.S. Appl. No. 17/230,203, Restriction Requirement mailed Sep. 8, 2023", 7 pgs.

"Chinese Application Serial No. 202110410953.5, Office Action mailed Jan. 4, 2024", W/English Translation, 11 pgs.

"Chinese Application Serial No. 202110410953.5, Response filed Feb. 19, 2024 to Office Action mailed Jan. 4, 2024", w/ English Claims, 11 pgs.

"Chinese Application Serial No. 202110410953.5, Response Filed Feb. 19, 2024 to Office Action mailed Jan. 4, 2024", W/ English Claims, 9 pgs.

"Australian Application Serial No. 2021202188, First Examination Report mailed Mar. 23, 2022", 4 pgs.

"Australian Application Serial No. 2021202188, Response filed Jul. 13, 2022 to First Examination Report mailed Mar. 23, 2022", 21 pgs.

"Canadian Application Serial No. 3,114,820, Examiner's Rule 86(2) Requisition mailed Jul. 13, 2022", 4 pgs.

"Canadian Application Serial No. 3,114,820, Response filed Nov. 8, 2022 to Examiner's Rule 86(2) Requisition mailed Jul. 13, 2022", 17 pgs.

"European Application Serial No. 21168687.8, Extended European Search Report mailed Dec. 20, 2021", 15 pgs.

"European Application Serial No. 21168687.8, Partial European Search Report mailed Sep. 16, 2021", 14 pgs.

"European Application Serial No. 21168687.8, Response filed Jul. 19, 2022 to Extended European Search Report mailed Dec. 20, 2021", 29 pgs.

"Simple Solutions for Precise Unicompartmental Knee Surgery", ORTHOsoft® Unicondylar Knee 1.0 Universal, User Manual, Zimmer CAS 853.00010E rev E, (2012), 38 pgs.

\* cited by examiner

DEVICES AND METHODS FOR POSTERIOR RESECTION IN ROBOTICALLY ASSISTED PARTIAL KNEE ARTHROPLASTIES

CLAIM OF PRIORITY

This application is a continuation-in-part of U.S. patent application Ser. No. 17/230,203, filed on Apr. 14, 2021, which claims the benefit of U.S. Provisional Patent Application Ser. No. 63/010,761, filed on Apr. 16, 2020. This application also claims the benefit of U.S. Provisional Patent Application Ser. No. 63/435,733, filed on Dec. 28, 2022. The benefit of priority of each of which are claimed hereby, and each of which are incorporated by reference herein in their entirety.

TECHNICAL FIELD

The present disclosure is directed to devices and methods for use in performing knee arthroplasty, such as total or partial knee replacement procedures. In a particular example, the devices and methods can be used to perform posterior resections.

BACKGROUND

Imaging of anatomical features can be useful in preparing for and performing surgical procedures. For example, patient-specific instruments can be derived from patient imaging and robotic surgical systems can be configured to track anatomy of a patient based on registration with patient imaging.

Patient-specific instruments have been successfully deployed for many surgical procedures. By creating three-dimensional (3D) models of anatomy of a patient from medical images, surgeries can be customized using virtual 3D surgical planning for specific patients. The virtual 3D surgical planning can be used to produce patient-specific cutting guides and instruments, which fit over the anatomy of the specific patient in a unique way to allow for precise replication of the planned surgery as compared to arthroplasty with conventional or standard instrumentation.

In robotic surgical systems, the shape of the anatomy in the patient imaging can be registered with another frame of reference, such as the physical space of an operating room where the robotic surgical system is located. Robotic surgical arms can be used to hold various instruments in place in a desired orientation relative to both the anatomy and operating room during a procedure so that movement of an instrument in the operating room relative to the anatomy can be tracked on the anatomic imaging based on movement of the robotic surgical arm. It is, therefore, desirable to precisely mount instruments to the robotic surgical arm.

Both patient-specific and robotic surgical procedures have been applied to knee arthroplasty procedures. Total and partial knee arthroplasties can be complicated procedures that utilize a plurality of different instruments that are switched during the procedure and result in the anatomy being repositioned throughout the procedure, thereby increasing the time and cost of the procedure. U.S. Pat. No. 10,136,952 to Couture et al. and Pub. No. US 2018/0116740 to Gogarty et al. describe cutting guides and instruments for use in knee replacement surgery.

OVERVIEW

The present inventors have recognized, among other things, that problems to be solved with traditional partial knee arthroplasties involve positioning of the knee joint in alignment to receive a prosthetic device that engages the tibia bone and the femur bone. As such, the depth of the resections of the tibia bone and femur bone must be coordinated to ensure a gap height for proper seating of the prosthetic device throughout flexion of the knee joint. Maintaining gap height in conventional procedures can be difficult as different guides and instruments are moved into and out of the surgical site for different resections, such as a distal cut and a posterior cut of the femur bone and a proximal and sagittal cut of the tibia bone.

The present inventors have also recognized, among other things, that problems to be solved with traditional partial knee arthroplasties include the need for having to attach multiple instruments for properly resecting the tibia bone and the femur bone, particularly the posterior portion of only one condyle in a partial knee arthroplasty. Each of these instruments needs to be properly aligned with the knee joint to, among other things, ensure proper gap height. Use of too many instruments can be off-putting for surgeons due to increased complexity and time of the surgeries. Furthermore, surgeries that require multiple instruments have conventionally been unsuitable for robot-assisted surgeries due to complexities of having to attach multiple instruments to the robotic surgical arm and the need to register each of these instruments individually.

The present subject matter can provide a solution to these and other problems, such as by providing solutions for allowing surgeons or surgical planners to plan gap height control for posterior resection of a single condyle in a partial knee arthroplasty. The solutions can include one or more of the following options: A) use robotic surgery planning software to adjust an extension gap to suit a flexion gap to manually position a manual posterior cut guide or to facilitate robotic placement of a posterior cut guide; B) use a surgical navigation system to determine a femur rotation axis to properly manually position a manual posterior cut guide or to facilitate robotic placement of a posterior cut guide; C1) use shims to adjust the position of a manual posterior cut guide; C2) use a robotically-guided femur and tibia partial cut guide block to position a robot-configured posterior cut guide relative to the distal end of a femur; and D) use a robotically-guided femur and tibia partial cut guide block to guide pin holes for a robot-configured posterior cut guide relative to the distal end of a femur. In additional examples, the present subject matter can provide solutions to these and other problems, such as by providing methods for digitizing the position of a robotically controlled posterior resection guide involving inserting a gap checker into a gap between a proximally resected tibia and a posterior portion of a condyle of a femur to set a gap height and femoral rotation and digitally correlate such gap height to the location for a robotically-positioned posterior resection guide to perform a posterior resection to achieve the same gap height and femoral rotation.

In an example, a method for aligning a posterior resection guide with a distal femur surface can comprise positioning a posterior resection guide adjacent a proximal resected surface of a tibia and a posterior surface of a femur for a knee joint in flexion, displaying a representation of a distal end of the femur on graphical display, displaying an alignment axis on the representation, engaging a tracking device to the posterior resection guide, tracking an anterior tip of the posterior resection guide on a graphical display, and rotating the posterior resection guide to align the anterior tip with the alignment axis on the graphical display.

In an additional example, a system for performing femoral resections for a partial knee arthroplasty can comprise a surgical robot comprising an articulating arm configured to move within a coordinate system for the surgical robot, a femoral resection guide instrument comprising, a coupler for connecting to the articulating arm, an extension arm extending from the coupler, and a resection block attached to the extension arm, and a finishing guide for performing a posterior resection of a distal femur, wherein the finishing guide is positionable by the surgical robot to determine a thickness and rotation of the posterior cut.

In another example, a method for resecting a distal femur for a partial knee arthroplasty can comprise attaching a resection guide instrument to an articulating arm of a robotic surgical system, moving the resection guide instrument to an anterior or posterior side of a distal end of a femur, resecting the distal end of the femur to form a distal resection surface, moving the resection guide instrument to the distal resection surface, drilling holes into the distal resection surface through the guide bores in the resection guide instrument, inserting pins into the drilled holes, attaching a finishing guide to the inserted pins, and resecting a posterior side of the femur adjacent the distal resection surface using the finishing guide to guide a cutting instrument.

In a further example, a method for aligning a posterior resection guide with a distal resected femur surface can comprise positioning a posterior resection guide adjacent the distal resected femur surface, inserting a flange of the posterior resection guide between a posterior surface of a femur and a proximal resected surface of a tibia, moving the posterior resection guide medial-laterally to observe a rim thickness between an anterior edge of the posterior resection guide relative to an edge of the distal resected femur surface, and positioning shims adjacent the flange to vary the rim thickness.

In yet another example, a system for performing femoral resections for a partial knee arthroplasty can comprise a surgical robot, a tracking system, a tracker, a finishing guide and a controller. The surgical robot can comprise an articulating arm configured to move within a coordinate system for the surgical robot. The tracking system can be configured to determine locations of one or more trackers in the coordinate system. The tracker can be configured to be tracked by the tracking system. The finishing guide can be configured to be coupled to the articulating arm to perform a posterior resection of a distal femur. The controller for the surgical robot can comprise a communication device configured to receive data from and transmit data to the surgical robot and the tracking system, a display device for outputting visual information from the surgical robot and the tracking system, and a non-transitory storage medium having computer-readable instructions stored therein comprising marking digital locations at a distal end and a posterior surface of a distal end of a femur using the tracker, displaying the digital locations of the distal end and posterior surface on the display device, plotting a target axis extending through the distal end and the posterior surface on the display device, projecting the target axis to an anterior surface of the femur, and moving the articulating arm to align the finishing guide along the target axis.

In additional examples, a method of positioning a posterior resection guide in a three-dimensional coordinate system using a robotic arm in order to perform a partial knee arthroplasty can comprise connecting a first tracking device for a surgical tracking system of the robotic arm to a femur, connecting a second tracking device for the surgical tracking system of the robotic arm to a tibia, manually positioning the tibia relative to the femur to a desired orientation to perform a posterior resection, manually determining a position for the posterior resection guide to perform the posterior resection, digitizing a reference point for the posterior resection guide in the three-dimensional coordinate system for a location of a feature of the posterior resection guide, moving the posterior resection guide to the location in the three-dimensional coordinate system with the robotic arm, and resecting a posterior portion of a condyle of the femur using the posterior resection guide to guide a cutting instrument.

DETAILED DESCRIPTION

Figure 1:
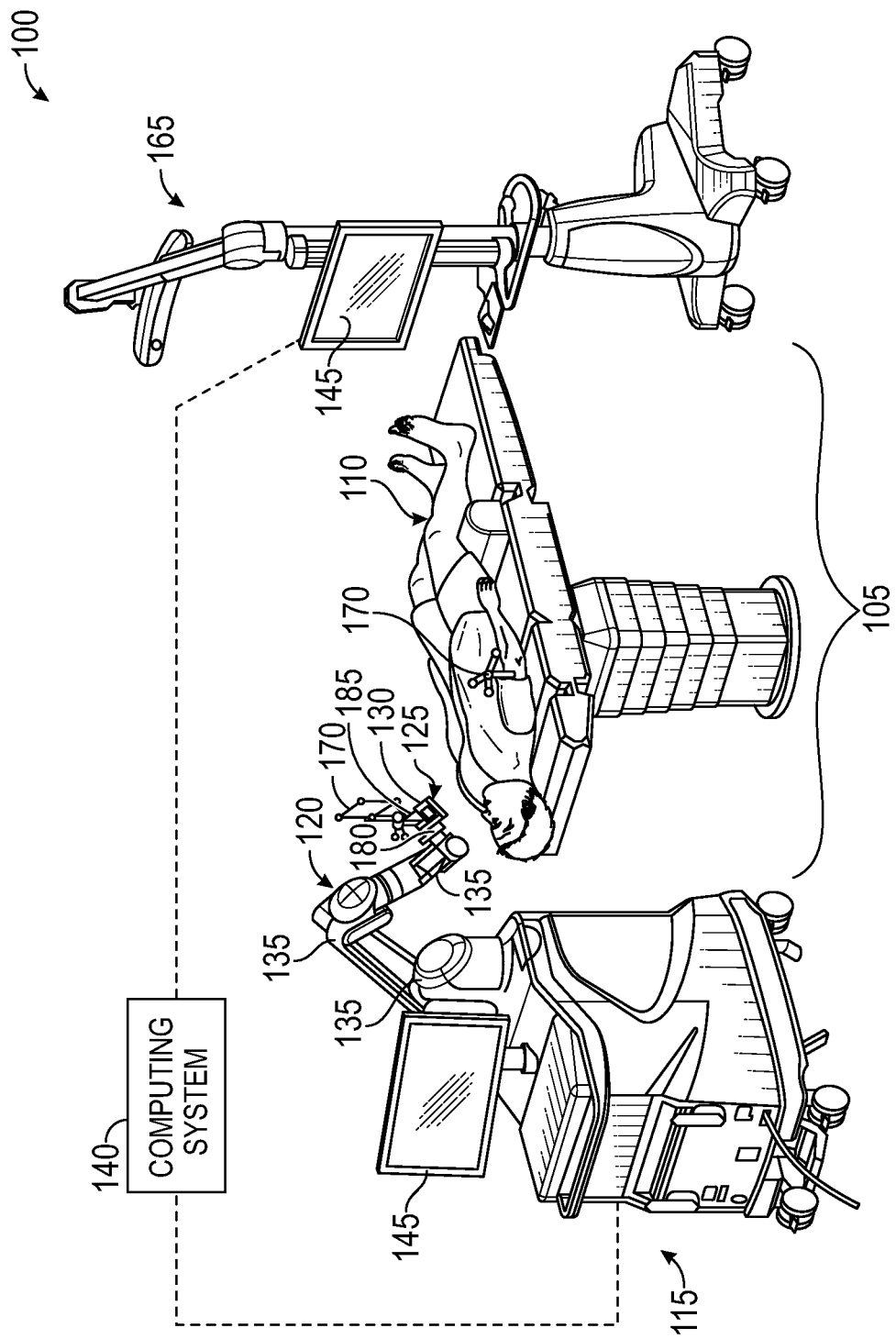
FIG. 1 is a diagrammatic view of an operating room including a robot-assisted surgical system comprising a robotic arm, a computing system and a tracking system.

FIG. 1 illustrates surgical system 100 for operation on surgical area 105 of patient 110 in accordance with at least one example of the present disclosure. Surgical area 105 in one example can include a joint and, in another example, can be a bone. Surgical area 105 can include any surgical area of patient 110, including but not limited to the shoulder, knee, head, elbow, thumb, spine, and the like. Surgical system 100 can also include robotic system 115 with one or more robotic arms, such as robotic arm 120. As illustrated, robotic system 115 can utilize only a single robotic arm. Robotic arm 120 can be a 6 degree-of-freedom (DOF) robot arm, such as the ROSA® robot from Medtech, a Zimmer Biomet Holdings, Inc. company. In some examples, robotic arm 120 is cooperatively controlled with surgeon input on the end effector or surgical instrument, such as surgical instrument 125. In other examples, robotic arm 120 can operate autonomously. While not illustrated in FIG. 1, one or more positionable surgical support arms can be incorporated into surgical system 100 to assist in positioning and stabilizing instruments or anatomy during various procedures.

Figure 2:
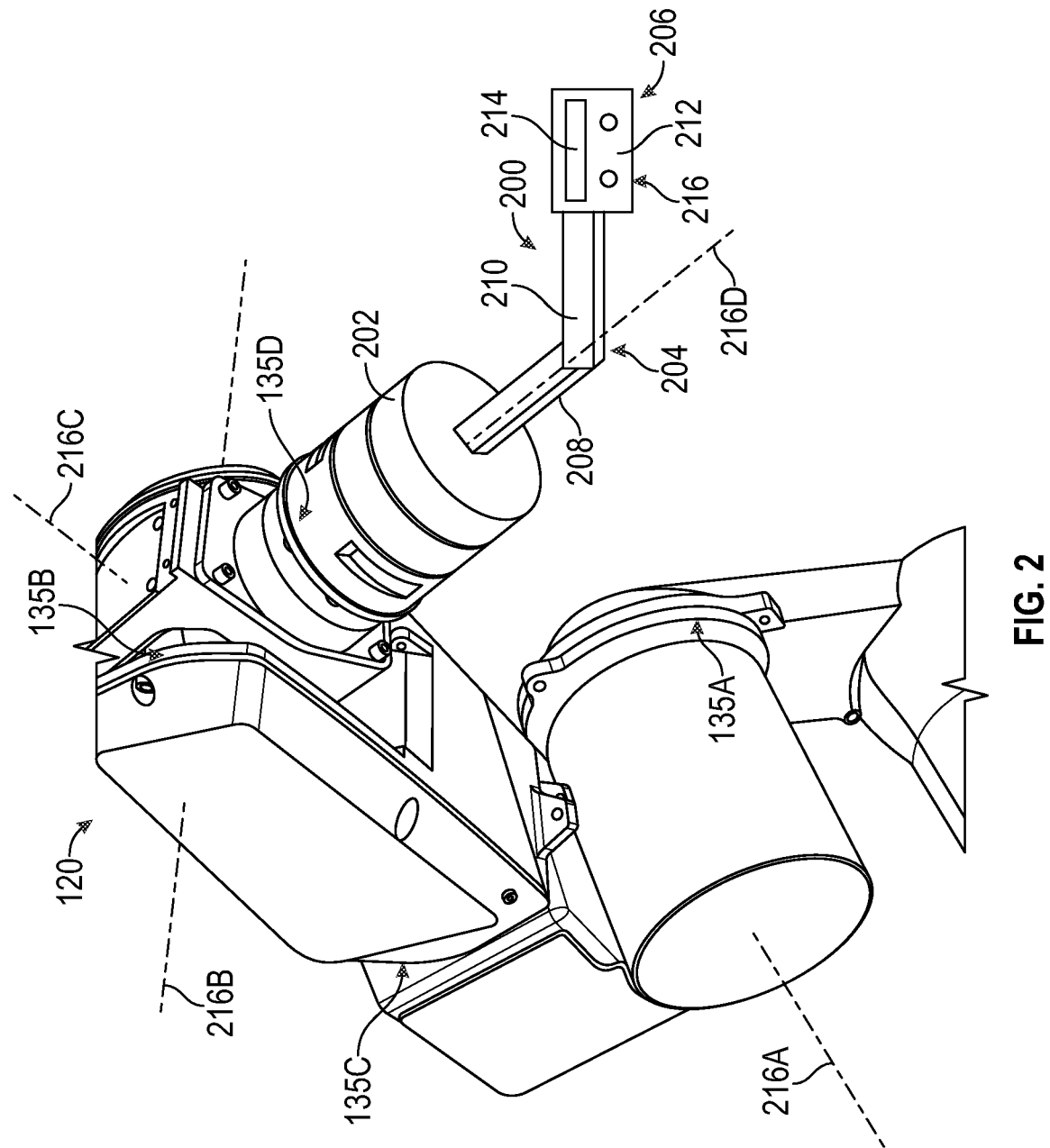
FIG. 2 is a schematic view of the robotic arm of FIG. 1 including a resection instrument configured to provide cutting guide functions and serve as a platform for mounting components for additional surgical steps, such as can be used to perform a partial knee arthroplasty.

Each robotic arm 120 can rotate axially and radially and can receive a surgical instrument, or end effector, 125 at distal end 130. Surgical instrument 125 can be any surgical instrument adapted for use by the robotic system 115, including, for example, a guide tube, a holder device, a gripping device such as a pincer grip, a burring device, a reaming device, an impactor device such as a humeral head impactor, a pointer, a probe, a cutting guide, an instrument guide, an instrument holder or a universal instrument adapter device as described herein or the like. Surgical instrument 125 can be positionable by robotic arm 120, which can include multiple robotic joints, such as joints 135, that allow surgical instrument 125 to be positioned at any desired location adjacent or within a given surgical area 105. As discussed below, robotic arm 120 can be used with posterior resection guide 300 of FIGS. 3A-3D to perform a partial knee arthroplasty using resection guide instrument 200 (FIG. 2). Robotic arm 120 can additionally be used with the instruments of FIGS. 4A-4D and FIGS. 5A and 5B. Furthermore, the surgical planning interface of FIG. 6 can be used in conjunction with robotic arm 120.

Robotic system 115 can also include computing system 140 that can operate robotic arm 120 and surgical instrument 125. Computing system 140 can include at least memory, a processing unit, and user input devices, as will be described herein. Computing system 140 and tracking system 165 can also include human interface devices 145 for providing images for a surgeon to be used during surgery. Computing system 140 is illustrated as a separate standalone system, but in some examples computing system 140 can be integrated into robotic system 115. Human interface devices 145 can provide images, including but not limited to three-dimensional images of bones, including tibia T and femur F of FIGS. 9-12, glenoids, knees, joints, and the like. Human interface devices 145 can include associated input mechanisms, such as a touch screen, foot pedals, or other input devices compatible with a surgical environment.

Computing system 140 can receive pre-operative, intraoperative and post-operative medical images. These images can be received in any manner and the images can include, but are not limited to, computed tomography (CT) scans, magnetic resonance imaging (MRI), two-dimensional x-rays, three-dimensional x-rays, ultrasound, and the like. These images in one example can be sent via a server as files attached to an email. In another example the images can be stored on an external memory device such as a memory stick and coupled to a USB port of the robotic system to be uploaded into the processing unit. In yet other examples, the images can be accessed over a network by computing system 140 from a remote storage device or service.

After receiving one or more images, computing system 140 can generate one or more virtual models related to surgical area 105. Alternatively, computing system 140 can receive virtual models of the anatomy of the patient prepared remotely. Specifically, a virtual model of the anatomy of patient 110, including tibia T and femur F of FIGS. 9-12, can be created by defining anatomical points within the image(s) and/or by fitting a statistical anatomical model to the image data. The virtual model, along with virtual representations of implants and instruments such as posterior resection guide 430 of FIGS. 4C and 4D, posterior resection guide 500 of FIG. 5A, posterior resection guide 300 of FIGS. 3B and 12 and gap checkers 802 and 860 of FIGS. 9-11, can be used for calculations related to the desired location, height, depth, inclination angle, or version angle of an implant, stem, acetabular cup, glenoid cup, total ankle prosthetic, total and partial knee prosthetics, surgical instrument, or the like to be utilized in surgical area 105. In another procedure type, the virtual model can be utilized to determine resection locations on femur and tibia bones for a partial knee arthroplasty, such as the location of virtual cut plane 848 of FIGS. 9 and 10. In a specific example, the virtual model can be used to determine a gap height for posterior femoral resections (e.g., posterior cut and chamfer cuts) relative to a proximally resected tibia. The virtual model can also be used to determine bone dimensions, implant dimensions, bone fragment dimensions, bone fragment arrangements, and the like. Any model generated, including three-dimensional models, can be displayed on human interface devices 145 for reference during a surgery or used by robotic system 115 to determine motions, actions, and operations of robotic arm 120 or surgical instrument 125. Known techniques for creating virtual bone models can be utilized, such as those discussed in U.S. Pat. No. 9,675,461, titled "Deformable articulating templates" or U.S. Pat. No. 8,884,618, titled "Method of generating a patient-specific bone shell" both by Mohamed Rashwan Mahfouz, as well as other techniques known in the art.

Computing system 140 can also communicate with tracking system 165 that can be operated by computing system 140 as a stand-alone unit. Surgical system 100 can utilize the Polaris optical tracking system from Northern Digital, Inc. of Waterloo, Ontario, Canada. Additionally, tracking system 165 can comprise the tracking system shown and described in Pub. No. US 2017/0312035, titled "Surgical System Having Assisted Navigation" to Brian M. May, which is hereby incorporated by this reference in its entirety. Tracking system 165 can monitor a plurality of tracking elements, such as tracking elements 170, affixed to objects of interest to track locations of multiple objects within the surgical field. Tracking system 165 can function to create a virtual three-dimensional coordinate system within the surgical field for tracking patient anatomy, surgical instruments, or portions of robotic system 115. Tracking elements 170 can be tracking frames including multiple IR reflective tracking spheres, or similar optically tracked marker devices. In one example, tracking elements 170 can be placed on or adjacent one or more bones of patient 110. In other examples, tracking elements 170 can be placed on robotic arm 120, surgical instrument 125, and/or an implant to accurately track positions within the virtual coordinate system associated with surgical system 100. In each instance tracking elements 170 can provide position data, such as patient position, bone position, joint position, robotic arm position, implant position, or the like. Examples of tracking elements suitable for use with computing system 140 can include tracker device 842 and tracker device 846 of FIG. 9, tracker device 854 of FIG. 10, tracker device 874 of FIG. 11, and tracker device 884 of FIG. 12.

Robotic system 115 can include various additional sensors and guide devices. For example, robotic system 115 can include one or more force sensors, such as force sensor 180. Force sensor 180 can provide additional force data or information to computing system 140 of robotic system 115. Force sensor 180 can be used by a surgeon to cooperatively move robotic arm 120. For example, force sensor 180 can be used to monitor impact or implantation forces during certain operations, such as insertion of an implant stem into a humeral canal. Monitoring forces can assist in preventing negative outcomes through force fitting components. In other examples, force sensor 180 can provide information on soft-tissue tension in the tissues surrounding a target joint. In certain examples, robotic system 115 can also include laser pointer 185 that can generate a laser beam or array that is used for alignment of implants during surgical procedures.

In order to ensure that computing system 140 is moving robotic arm 120 in a known and fixed relationship to surgical area 105 and patient 110, the space of surgical area 105 and patient 110 can be registered to computing system 140 via a registration process involving registering fiducial markers attached to patient 110 with corresponding images of the markers in patient 110 recorded preoperatively or just prior to a surgical procedure. For example, a plurality of fiducial markers, such as first tracker 806 and second tracker 810 of FIG. 9, can be attached to patient 110, images of patient 110 with the fiducial markers can be taken or obtained and stored within a memory device of computing system 140. Subsequently, patient 110 with the fiducial markers can be moved into, if not already there because of the imaging, surgical area 105 and robotic arm 120 can touch each of the fiducial markers. Engagement of each of the fiducial markers can be cross-referenced with, or registered to, the location of the same fiducial marker in the images. In additional examples, patient 110 and medical images of the patient can be registered in real space using contactless methods, such as by using a laser rangefinder held by robotic arm 120 and a surface matching algorithm that can match the surface of the patient from scanning of the laser rangefinder and the surface of the patient in the medical images. As such, the real-world, three-dimensional geometry of the anatomy attached to the fiducial markers can be correlated to the anatomy in the images and movements of instrument 125 attached to robotic arm 120 based on the images will correspondingly occur in surgical area 105.

Subsequently, other instruments and devices attached to surgical system 100 can be positioned by robotic arm 120 into a known and desired orientation relative to the anatomy. For example, robotic arm 120 can be coupled to resection guide instrument 200 of FIG. 2, posterior resection guide 430 of FIGS. 4C and 4D, and posterior resection guide 500 of FIG. 5A, that can be used to guide resections on multiple bones (e.g., proximal tibia and distal femur) and that allows other instruments (e.g., a finishing guide or posterior cut guide) to be attached to robotic arm without having to individually couple each instrument to robotic arm in succession and without the need for individually registering each attached instrument with the coordinate system. As discussed with reference to FIGS. 7 and 8, memory for computing system 140, e.g., memory 1704, can include geometric information for instruments and gap checkers described herein so that the specific location of each instrument and gap checker, and specific features thereof, can be determined and known by computing system 140 when attached to robotic arm 120. Robotic arm 120 can move resection guide instrument 200 relative to anatomy of the patient such that the surgeon can, after adding and removing another instrument to the guide instrument as needed, perform the desired interaction with the patient at specific locations called for by the surgical plan with the attached instrument.

FIG. 2 is a schematic view of robotic arm 120 of FIG. 1 including resection guide instrument 200, which can be positioned by robotic arm 120 relative to surgical area 105 (FIG. 1) in a desired orientation according to a surgical plan, such as a plan based on preoperative imaging or based, at least partially, on intra-operative planning such as is described with reference to FIG. 3D. Resection guide instrument 200 can comprise tool base 202, extension arm 204 and guide block 206. Extension arm 204 can comprise first segment 208 and second segment 210, as well as additional segments in other examples. Guide block 206 can comprise body 212, guide surface 214 and interface 216. In an example, guide block 206 can be configured as a resection block for use in a partial knee arthroplasty and, as such, guide block 206 can be used to perform a proximal resection of a tibial plateau and a distal resection of a femoral condyle. Further, other instruments, such as posterior resection guide 430 (FIG. 4C) and posterior resection guide 500 (FIG. 5A), can be coupled to guide block 206.

Robotic arm 120 can include joint 135A that permits rotation about axis 216A, joint 135B that can permit rotation about axis 216B, joint 135C that can permit rotation about axis 216C and joint 135D that can permit rotation about axis 216D.

In order to position resection guide instrument 200 relative to anatomy of patient 110 (FIG. 1), surgical system 100 (FIG. 1) can manipulate robotic arm 120 automatically by computing system 140 or a surgeon manually operating computing system 140 to move resection guide instrument 200 to the desired location, e.g., a location called for by a surgical plan to align an instrument relative to the anatomy. For example, robotic arm 120 can be manipulated along axes 216A-216D to position resection guide instrument 200 such that guide block 206 is located in a desired location relative to the anatomy. As such, a step of a surgical procedure can be performed, such as by using guide surface 214. However, subsequent steps of the surgical procedure can be performed with resection guide instrument 200 without having to uncouple instrument 200 from robotic arm 120. For example, other instruments can be attached to guide block 206 at interface 216. Other instruments attached at interface 216 can be used without having to re-register an additional instrument to the coordinate system because the dimensions and geometries of resection guide instrument 200 and other instruments to be used therewith, as well as other instruments and devices described herein with reference to FIGS. 3A-5B and 9-12, can be known by surgical system 100 (FIG. 1), such as by having physical dimensions for geometries of such devices being stored in memory, such that the locations of guide block 206 and instruments attached thereto can be calculated by surgical system 100 as robotic arm 120 moves throughout the coordinate system. Stated another way, the location of axis 216A within surgical area 105 can be known to computing system 140. The location of tool base 202 within surgical area 105 can be calculated based on computing system 140 knowing the dimensions of robotic arm 120 and the relative positions portions of robotic arm 120 at axes 216A, 216B, 216C and 216D. The locations of instruments attached to tool base 202 can be known to computing system 140 based on computing system 140 knowing the dimensions and shape of each instrument.

Figure 7:
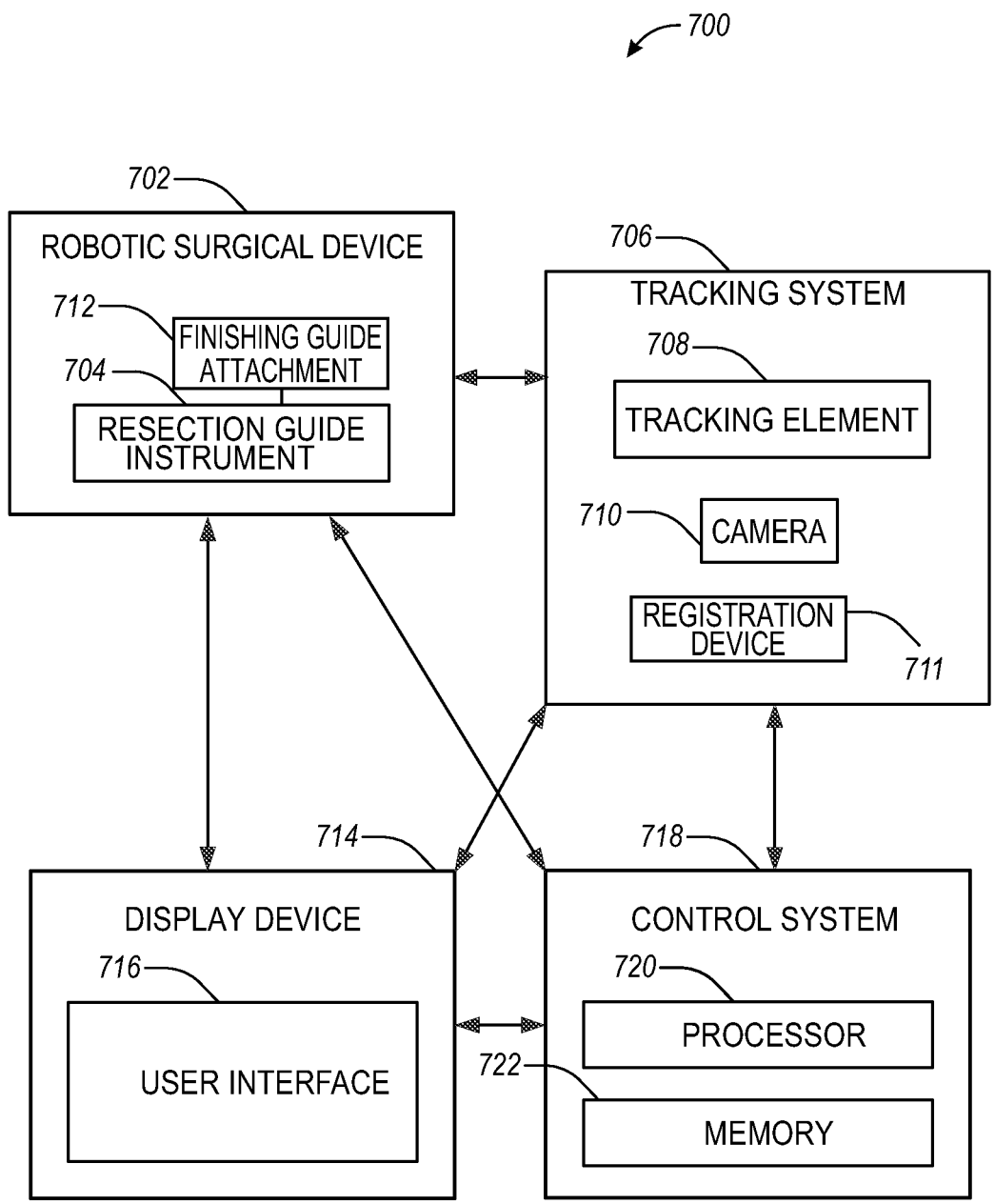
FIG. 7 is a schematic illustration of a robotic surgical system incorporating a resection guide instrument and finishing guide adapter of the present application interacting with a tracking system.

Robotic arm 120 can be separately registered to the coordinate system of surgical system 100, such via use of a tracking element 170 (FIG. 1). Fiducial markers can additionally be separately registered to the coordinate system of surgical system 100 via engagement with a probe having a tracking element 170 attached thereto. Resection guide instrument 200 can be registered to the coordinate system via coupling with robotic arm. Other components, such as pointer 326 (FIGS. 3B and 3C) and posterior resection guide (FIGS. 4C and 4D), can be registered using tracking elements 170 (FIG. 1) and tracking element 708 (FIG. 7). As such, some or all of the components of surgical system 100 can be individually registered to the coordinate system (with or without the aid of tracking elements) and, if desired, movement of such components can be continuously or intermittently tracked with a tracking element 170.

In some robotic procedures, instruments can be separately and individually tracked using an optical navigation system that, under ideal conditions, alleviate the need for precisely maintaining axis 216D and the location of an instrument along axis 216D through a surgical procedure or surgical task, as the optical navigation system can provide the surgical computer system information to compensate for any changes. However, as optical navigation systems require line-of-sight with the instruments to be maintained, there is a significant advantage in not requiring instruments to be navigated (or at least not constantly navigated). Resection guide instrument 200 allows multiple instruments to be registered to robotic system 115 without the need for individually tracking each instrument. Robotic system 115 can know the precise location of robotic arm 120, and the geometry and dimensions of resection guide instrument 200 can be registered to robotic system 115, such as by being in communication with computing system 140. As such, the location of guide block 206 in the surgical space can be determined as robotic arm 120 moves guide block 206 within the surgical space. Furthermore, robotic system 115 can be provided, such as within a non-transient computer-readable storage medium, with the geometry and dimensions of instruments configured to be attached to guide block 206 such that the locations of attachment instruments can also be tracked as robotic arm 120 moves. Thus, individual tracking or registration of the attachment instruments can be avoided if desired.

Figure 3A:
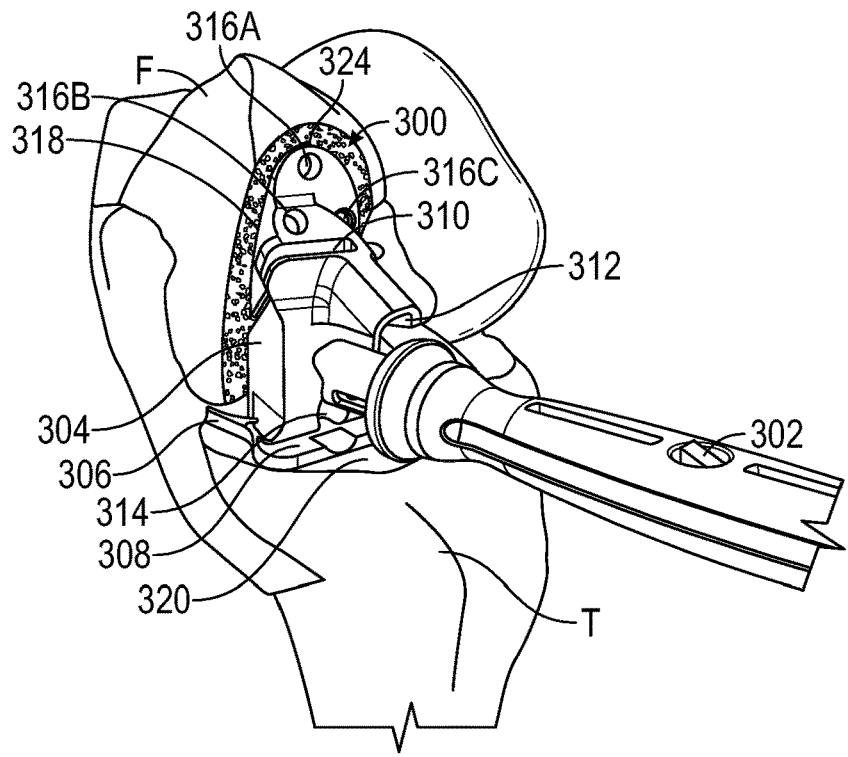
FIG. 3A is a perspective view of a posterior resection guide inserted between a femur and a tibia of a knee joint of a patient.
Figure 3B:
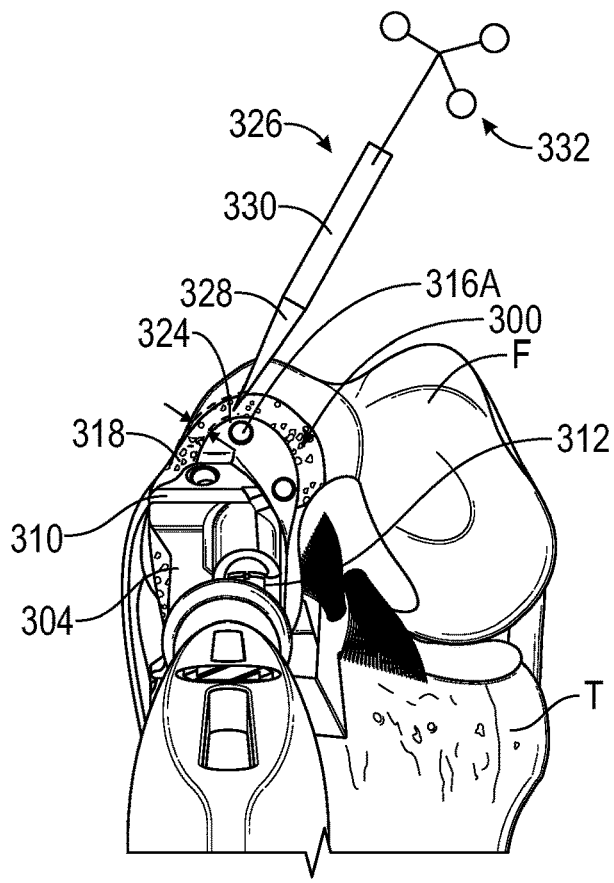
FIG. 3B is a front view of the posterior resection guide of FIG. 3A inserted between the femur and the tibia.
Figure 3C:
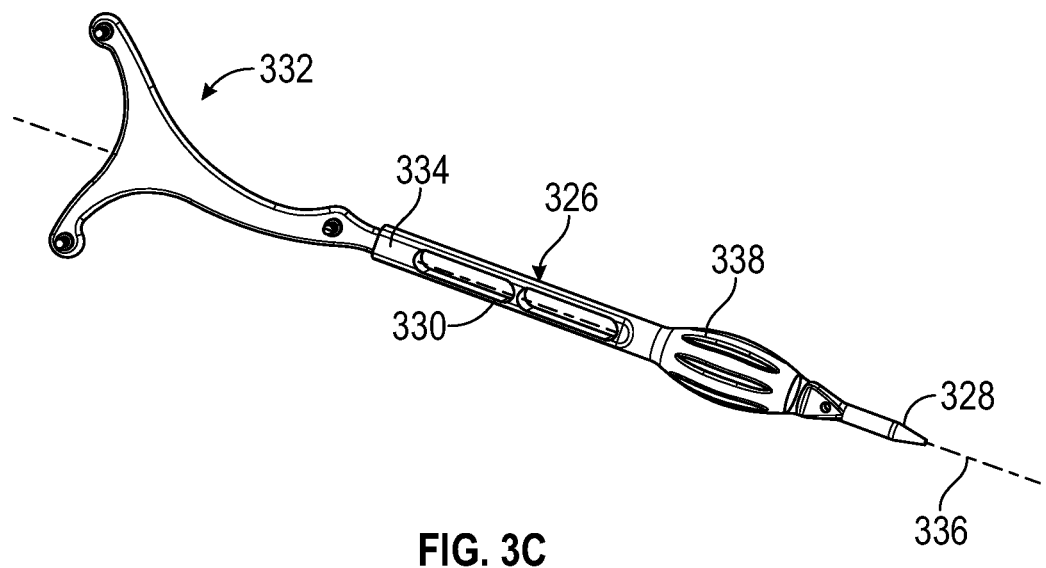
FIG. 3C is a perspective view of a pointer connected to a tracking device.
Figure 3D:
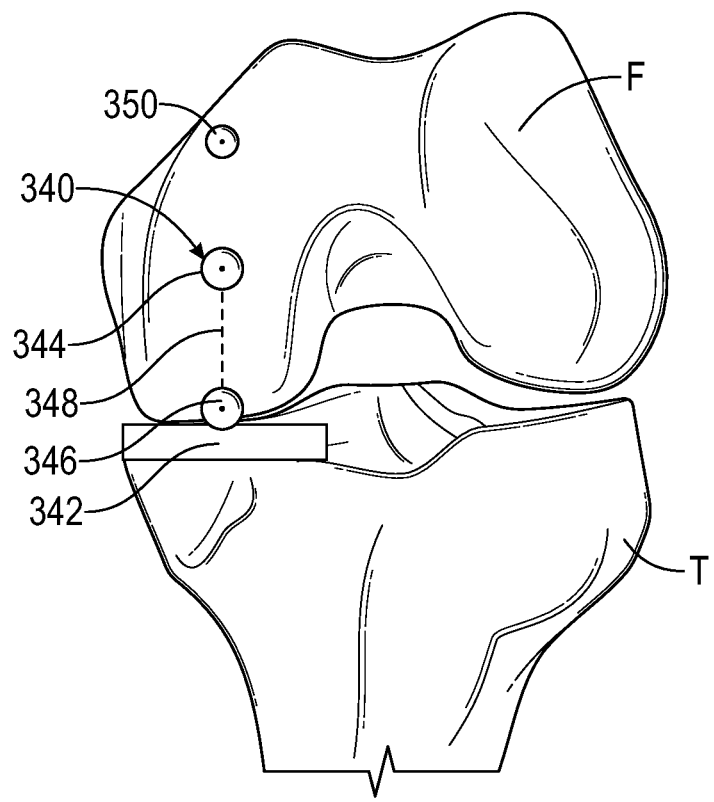
FIG. 3D shows a target axis illustrated on the distal end of the femur F.

FIGS. 3A-3D illustrate instruments and methods for determining a femur rotation axis for a partial knee arthroplasty. FIGS. 3A-3D illustrate devices and methods for using use a surgical navigation system to determine a femur rotation axis to properly manually position a posterior cut guide or to facilitate robot-guided posterior cut guide placement, which in turn allows from proper rotational positioning of a femoral implant. In a specific example, the posterior resection cut guide can be a device configured to be manually positioned and aligned. Typically, such devices are aligned using surgeon skill and experience by visually evaluating the position of the device relative to the distally resected femur. FIG. 3D illustrates a method for using a navigation system to determine an axis along the femur that can be used to align the posterior cut guide manually or with the aid of a robot.

FIG. 3A is a perspective view of posterior resection guide 300 inserted between femur F and tibia T. Handle 302 can be connected to posterior resection guide 300. In the illustrated example, posterior resection guide 300 comprises a uni-condylar resection guide configured to guide a resection along a posterior portion of a single condyle at a distal end of femur F. Posterior resection guide 300 can comprise body 304 and flange 306. Body 304 can be configured for coupling to handle 302, such as by including a socket or adapter that receives a mating component on handle 302. Body 304 can additionally include features for guiding cutting instruments or other instruments against femur F. For example, body 304 can include posterior cut guide surface 308, chamfer cut guide surface 310, anterior peg guide hole 312, posterior peg guide hole 314 and pin holes 316A, 316B and 316C. Femur F includes distal resected surface 318 and tibia T includes proximal resected surface 320.

Posterior resection guide 300 can be inserted between femur F and tibia T such that flange 306 contacts proximal resected surface 320 and body 304 contacts distal resected surface 318. A set of posterior resection guides 300 can be provided with each having body 304 with different sizes configured to implant different sized prosthetic components for different sized bones. Posterior resection guide 300 can also be referred to as a finishing guide because other features of body 304 can be used to finish the distal end of femur F to receive a prosthetic device. For example, chamfer cut guide surface 310 can be used to perform a chamfer resection that forms an angled surface between resected surface 318 and the surface formed with cut guide surface 308. Also, guide holes 312 and 314 can be used to drill holes to receive fixation features, e.g., pegs, of a prosthetic device such as a uni-condylar prosthetic device. Pin holes 316A-316B can be used to insert pins or pegs into resected surface 318 to temporarily affix posterior resection guide 300 to femur F while the bone is being modified using posterior resection guide 300, such as to stabilize the cuts being performed.

FIG. 3B is a front view of posterior resection guide 300 inserted between femur F and tibia T. The location of posterior resection guide 300 can be visually inspected to determine the location of body 304 against distal resected surface 318 by evaluating the distance between the edge of distal resected surface 318 and body 304, which can affect the thickness of the posterior cut and resulting rotation of the femoral component. In examples, shims can be positioned adjacent flange 306 to vary the amount of bone that is resected along the posterior cut. For example, shims of predetermined thicknesses can be used individually or stacked to vary the distance between body 304 and the edge of resected surface 318, such as by placing the shims below flange 306. Additionally, shims can be positioned on top of flange 306 to vary the distance between the edge of distal resected surface 318 and body 304. In additional examples, flange 306 can be omitted from posterior resection guide 300, or as in other examples described herein, in order to allow for the use of shims without accommodating flange 306. When properly sized, there is typically a rim of at least 2 mm of exposed bone between the edge of distal resected surface 318 and body 304. However, sometimes it is difficult to evaluate the position of posterior resection guide 300 due to engagement between the non-resected condyle and the non-resected portion of the proximal end of tibia T causing a pivoting action between the resected portions, as well as tissue of the patient obstructing visibility. In the present disclosure, pointer 326 can be used to facilitate alignment of posterior resection guide 300, such as where anterior tip 324 is placed medial-laterally on distal resected surface 318 or where the outer profile of guide 300 sits on the distal resected surface 318.

FIG. 3C is a perspective view of pointer 326. Pointer 326 can comprise tip 328, shaft 330 and tracking device 332. Pointer 326 can comprise a device for contacting specific locations in the coordinate system of robotic system 115 (or computing system 140) using tracking device 332. Tracking device 332 can comprise a tracking array, such as tracking element 170 of FIG. 1, that can provide location information to robotic system 115. Tracking device 332 can be inserted into socket 334 and secured thereto by a pin or the like to fix the location of tracking device 332 relative to tip 328. Tip 328 can comprise a pointed end of shaft 330 that can be used to engage tissue of a patient to mark locations for the coordinate system of robotic system 115. In other examples, other instruments having preconfigured or fixed geometric shapes can be used in conjunction with a tracking device to mark locations for the coordinate system. Tip 328 can be pressed into bone, for example, while tracking device 332 provides a reading to surgical system 100. Thus, tracking device 332 can provide an indication of the location of pointer axis 336 to robotic system 115. Pointer 326 can further comprise handle 338. Handle 338 can provide an ergonomic grip for pointer 326 to allow manipulation by a surgeon. In order to increase the accuracy of the registration process, it is desirable for pointer shaft 330 to extend over a length to increase the location reading of axis 336 taken at tip 328. It is also desirable for handle 338 to be located close to tip 328 to allow a surgeon to easily place tip 328 where desired.

Posterior resection guide 300 can be engaged with pointer 326 to track the position and orientation of posterior resection guide 300 relative to femur F. In particular, pointer 326 can be used to align posterior resection guide 300 with target axis 340 (FIG. 3C) to facilitate aligning of posterior resection guide 300 for determining proper gap height.

FIG. 3D shows target axis 340 illustrated on distal end of femur F. In an example, target axis 340 could be determined preoperatively using imaging of the patient of femur F and tibia T using, for example, known techniques. In other examples according to the present disclosure, target axis 340 can be determined intra-operatively. Target axis 340 can be determined before the distal end of femur F is resected to remove any condyles. For example, target axis 340 can be determined before either of femur F and tibia T are resected, or after tibia T is resected to form proximal resected surface 320 and with shim 342 inserted therebetween.

Target axis 340 can comprise distal point 344 and posterior point 346. Distal point 344 can be determined, identified and marked with tibia T placed in extension relative to femur F. A physical mark can be placed on femur F or a digital mark can be placed on an image of femur F at the location where the tibia plateau of tibia T contacts the condyle of femur F using robotic system 115 (or computing system 140). A marker can be used to draw on femur F or a scoring device, such as a pin, can be used to scratch an indentation in femur F. Additionally, pointer 326 can be used to digitally mark the location of distal point 344 by engaging tip 328 with the engagement point between the tibial plateau and the condyle. Next, tibia T can be rotated into a flexion position relative to femur F such that posterior point 346 can be determined, identified and marked, either physically or digitally using a similar method as was used to mark distal point 344. Line 348 can be extended between distal point 344 and posterior point 346 to facilitate projection of the location for anterior point 350. The projection of line 348 can be followed up the anterior side of femur F to anterior point 350 to find the rotational, e.g., medial-lateral, location for anterior tip 324 for body 304 of posterior resection guide 300, which allows for proper rotational placement of a femoral implant installed according to drilled holes and the like with posterior resection guide 300. For example, pointer 326 can be engaged with tip 324 and posterior resection guide 300 can be internally-externally rotated until tip 324 is positioned on the extension of line 348 or the outer profile of guide 300 appropriately covers the distal resected surface 318, thereby indicating the proper position for posterior resection guide 300. For example, a digital representation of pointer axis 336 can be displayed on a user interface device (e.g., user or human interface device 145 of FIG. 1) to facilitate alignment with a digitally generated version of target axis 340 also shown on the user interface device. Also, the physical device of posterior resection guide 300 can be aligned with the physical line scored or drawn on femur F. In other examples, a tracking device such as pointer 326 can be directly coupled to posterior resection guide 300, rather than simply engaged with tip 324, such as by insertion into a socket or threaded bore, as explained in greater detail with reference to FIG. 12. Thus, 1) in a first example, line 348 and point 350 can be physically drawn on the distal end of the femur using a marking pen, the position of posterior resection guide 300 can be manually positioned by a surgeon against the femur, with or without the use of shims, and pointer 326 can be used to digitize the location of point 350 at anterior tip 324 to generate location information for the guidance of robotic arm 120 to position posterior resection guide 300, and 2) in a second example, a digital line (or plurality of discretely taken landmarks) can be drawn on the distal end of the femur using pointer 326 to digitize line 348 and point 350 on a display screen, the position of posterior resection guide 300 can be physically positioned by a surgeon while connected to tracker device 370 to move anterior tip 324 into alignment with point 350 on the display screen to generate location information for the guidance of robotic arm 120 to position posterior resection guide 300. Although described with reference to aligning anterior tip 324 with point 350, the description of FIGS. 3A-3D can be applied to appropriately locating and/or orienting any components described herein, such as cut guides, spacer blocks, shims and gap checkers. The procedures described herein can have the following goals: 1) aligning the femur perpendicular to the tibial component when in flexion, 2) sizing and locating the femur appropriately so as to not overhang the distal cut surface 318, and 3) rotating the femur to provide appropriate interior/exterior rotation to serve the needs of the patella.

Figure 4A:
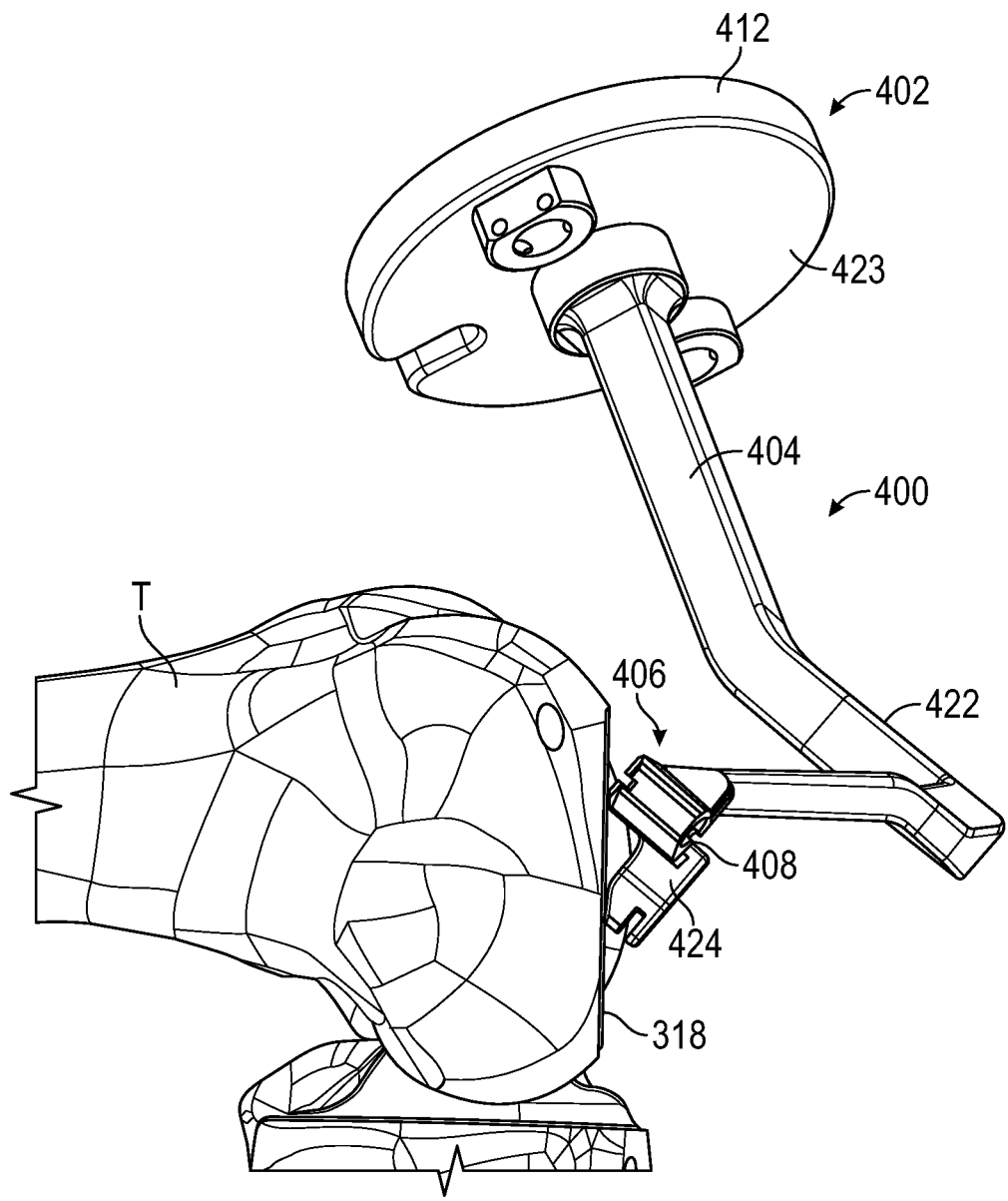
FIG. 4A is a side view of partial knee resection guide positioned against a resected distal end of a femur.
Figure 4B:
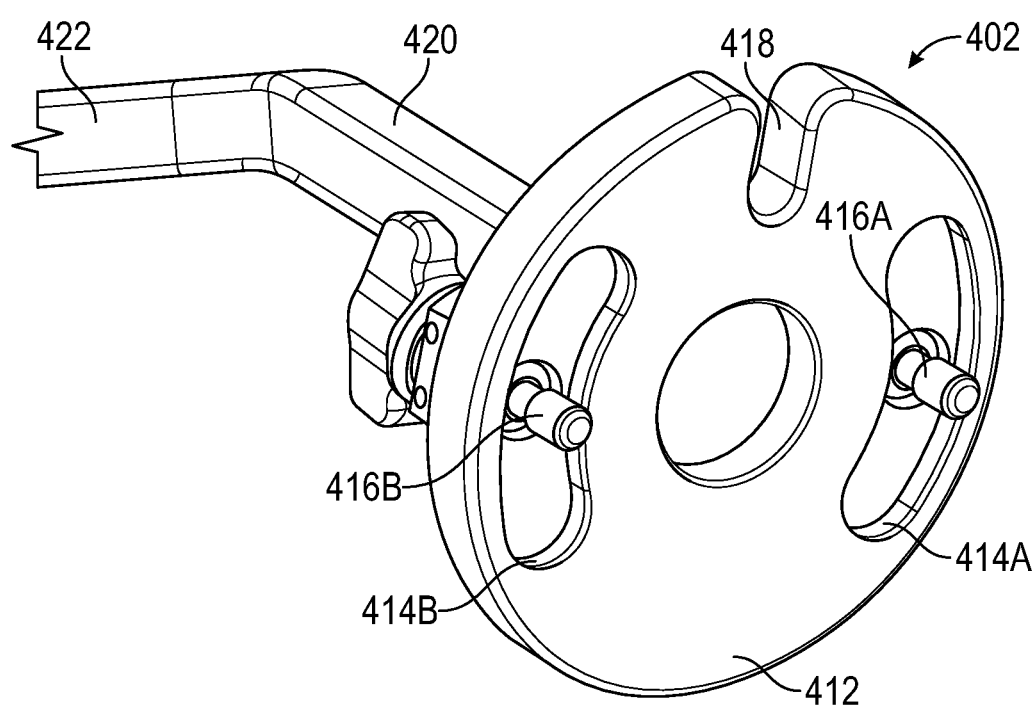
FIG. 4B is a perspective view of a tool base for the partial knee resection guide of FIG. 4A, which is attached to an extension arm.

FIG. 4A is a side view of partial knee resection guide 400 positioned against a resected distal end of femur F. FIG. 4B is a perspective view of tool base 402 of partial knee resection guide 400 attached to extension arm 404. FIGS. 4A and 4B are discussed concurrently. In examples, partial knee resection guide 400 can be configured similarly to cut guides disclosed in U.S. Pat. No. 10,136,952 to Couture et al. and Pub. No. US 2018/0116740 to Gogarty et al.

Figure 4C:
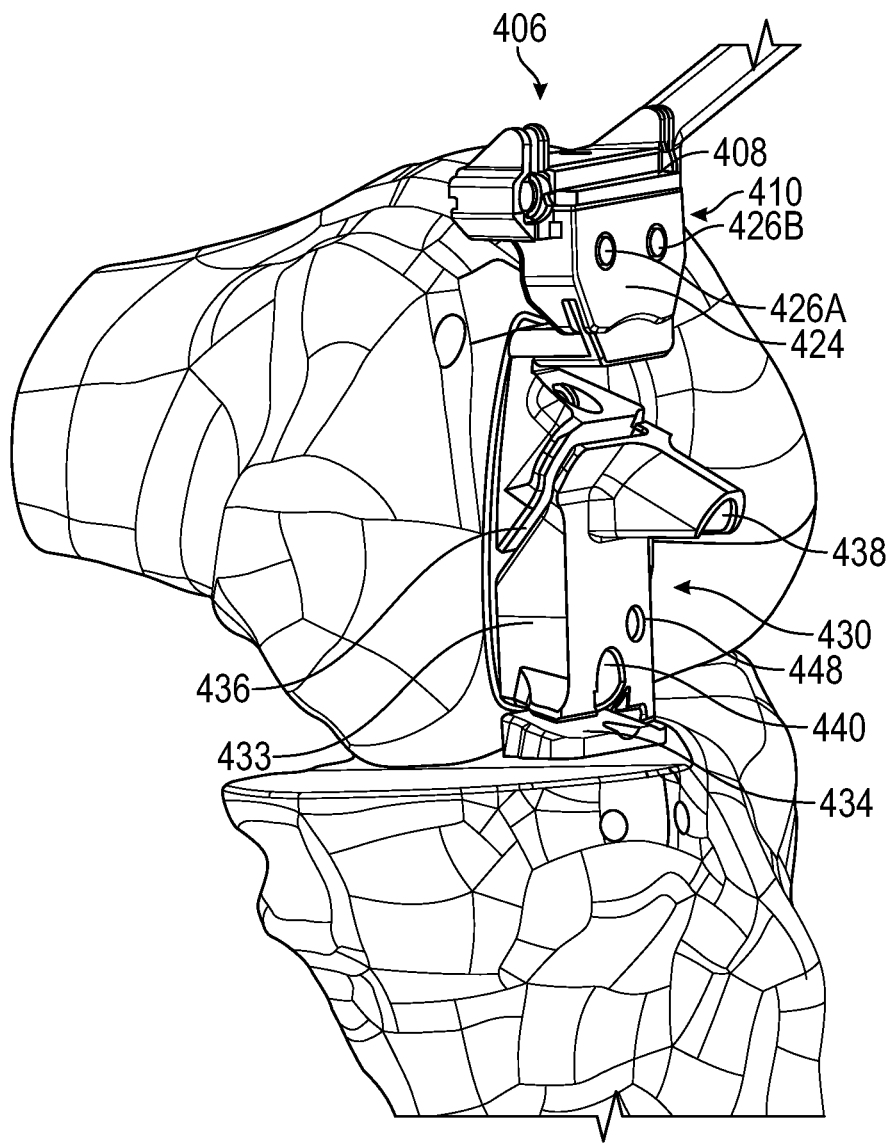
FIG. 4C is a perspective view of the posterior resection guide of FIG. 4A, which can be configured to include an attachment portion for coupling to a resection instrument.
Figure 5A:
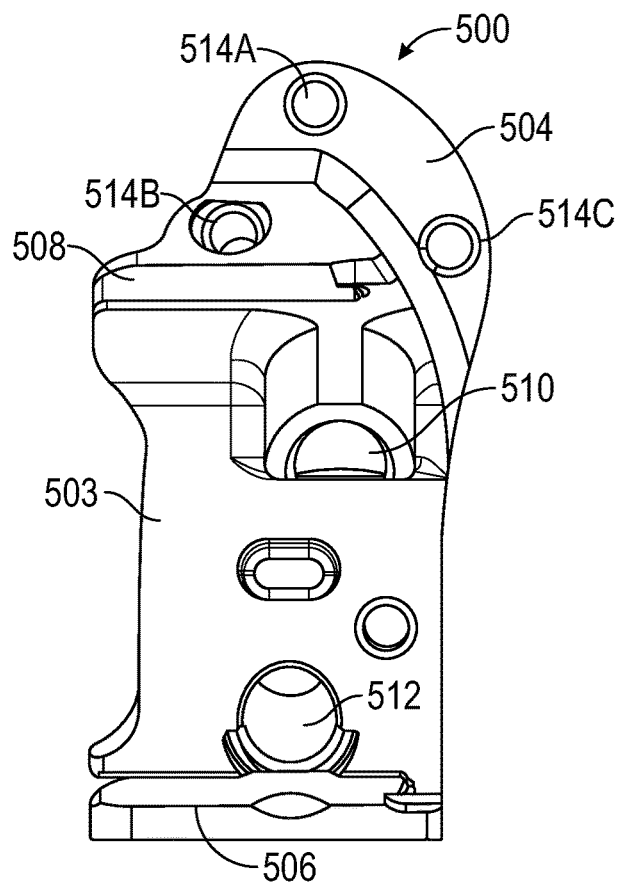
FIG. 5A is a front view of robot-configured posterior cut guide showing a coupling portion for connecting to a robotically-guided resection instrument.

Partial knee resection guide 400 can comprise tool base 402, extension arm 404 and resection block 406, which can comprise a resection block for resecting the distal portion of femur F, the proximal portion of tibia T and for mounting posterior resection guide 300 (FIGS. 3A-3B) and variations thereof (FIGS. 4C and 5A). Resection block 406 can comprise both an instrument and an adapter for attaching other instruments to extension arm 404 and, hence, robotic arm 120. For example, guide surface 408 can comprise a slot for guiding or otherwise engaging a cutting instrument such as a reciprocating or oscillating saw blade to cut bone, such as a superior portion of tibia T and a distal portion of femur F. Interface 410 (FIG. 4C) can comprise features that facilitate attachment of other instruments to resection block 406, such as ports, plugs, receptacles, threaded couplers, slots and the like. In examples, interface 410 (FIG. 4C) can comprise one or more through-bores, threaded bores, dovetail slots, pins, detents, chuck mechanisms and collets, and combinations thereof.

Tool base 402 (FIG. 4B) can comprise pedestal 412 from which extension arm 404 can extend, mounting slots 414A and 414B and fasteners 416A and 416B. Tool base 402 can be coupled to robotic arm 120 by inserting fasteners 416A and 416B through mounting slots 414A and 414B and into mating bores in robotic arm 120. Slot 418 can receive an alignment feature on robotic arm 120 to ensure proper mounting of tool base 402.

Extension arm 404 can comprise first segment 420 and second segment 422, as well as other segments to position resection block 406 relative to tool base 402. Segments 420 and 422 can comprise elongate rigid members extending from tool base 402 in an end-to-end fashion. Segments 420 and 422 can be configured to hold resection block 406 in a fixed position relative to tool base 402. Such positional relationship can be stored in a non-transient computer-readable storage medium for robotic system 115 or computing system 140. Segments 420 and 422 can be tubular or solid bodies that are angled relative to each other to position resection block 406 relative to tool base 402, such as in a position conducive for a surgeon to access resection block 406 while robotic arm 120 is out of the way of the surgeon. In an example, first segment 420 can extend from tool base 412 perpendicular, or approximately perpendicular, to front surface 423 of tool base 412 (FIG. 4A). In other examples, segments 420 and 422 can comprise curved segments. In various examples, segments 420 and 422 can lie in a common plane or can be in planes oblique to each other. Additionally, other distal segments at the end of segment 422 can taper down toward resection block 406 to reduce the footprint against resection block 506.

Resection block 406 can comprise body 424 that provides a platform for guide surface 408 and interface 410. Body 424 can further comprise bores 426A and 426B that can define interface 410 (FIG. 4C).

With reference to FIG. 4C, guide surface 408 can comprise a planar surface against which a cutting instrument can be engaged to perform a cutting procedure. In the illustrated example, guide surface 408 can comprise a slot that is bounded on four sides, e.g., front body 424 can provide upper, lower and lateral sides around guide surface 408. However, in other examples, guide surface 408 can comprise an unbounded ledge or a partially bounded ledge, e.g., a partial slot. Guide surface 408 can be located toward a side of body 424 to increase visibility of anatomy behind resection block 406. For example, guide surface 408 can be located proximate to a top surface such that a surgeon can view anatomy over the top of resection block 406 while simultaneously allowing the lower portion of body 424 to include bores 426A and 426B for interface 410. Guide surface 408 can be sized, e.g., have a width, suitable for resecting a single femoral condyle or half of a tibial plateau.

Bores 426A and 426B can comprise through bores extending from a front surface of body 424 all the way through to a rear surface of body 424. Bores 426A and 426B can thus provide ports for inserting pins through body 424 and into the anatomy of the patient. The pins can be used to, for example, anchor resection block 406 while cutting of bone occurs to ensure a straight cut. Additionally, bores 426A and 426B can comprise a portion of interface 410.

Interface 410 and guide surface 408 can also comprise means for facilitating coupling of another instrument to resection block 406. In other examples, interface 410 can comprise a socket having one or more receptacles for receiving mating components on an additional instrument. In the illustrated example, interface 410 can comprise bores 426A and 426B. Bores 426A and 426B can comprise multiple points of contact between resection block 406 and a mating instrument to facilitate rotational alignment. In examples, one or more of bores 426A and 426B can be threaded to receive a complimentary threaded shaft or fastener. For example, bores 426A and 426B can be threaded to receive a threaded fastener extending from an additional instrument or can be simple through-bores to receive alignment prongs of the additional instrument.

Figure 4D:
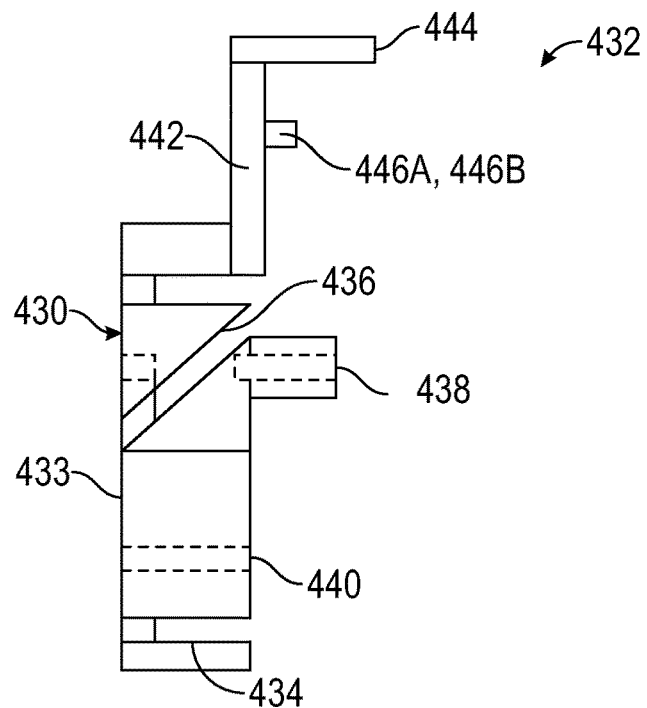
FIG. 4D is a diagrammatic side view of the posterior resection guide of FIG. 4C showing an attachment portion.

FIG. 4C is a perspective view of posterior resection guide 430 comprising attachment portion 432. FIG. 4D is a diagrammatic side view of posterior resection guide 430 of FIG. 4C. FIGS. 4C and 4D are discussed concurrently.

Posterior resection guide 430 can be configured similarly as posterior resection guide 300 of FIGS. 3A and 3B except for the omission of flange 306 and the inclusion of attachment portion 432. As such, posterior resection guide 430 can comprise body 433, posterior cut guide surface 434, chamfer cut guide surface 436, anterior peg guide hole 438 and posterior peg guide hole 440. Posterior resection guide 430 can include attachment portion 432 that can comprise superior extension 442, coupling flange 444 and tabs 446A and 446B. Attachment portion 432 can be used to couple posterior resection guide 430 to resection block 406. For example, coupling flange 444 can be inserted into guide surface 408 and/or tabs 446A and 446B can be inserted into bores 426A and 426B, respectively. Coupling flange 444 and tabs 446A and 446B can be used separately or together in various examples of posterior resection guide 430. In another example, one or both of coupling flange 444 and tabs 446A and 446B can be omitted and superior extension 442 can be inserted into a slot within body 424. Attachment portion 432 can be integral with body 433 or can be a separate component attached thereto.

Attachment portion 432 thus allows posterior resection guide 430 to be coupled to resection block 406 and, therefore, robotic arm 120. As such, posterior resection guide 430 can be robotically positioned within the coordinate system of robotic arm 120 relative to femur F, thereby eliminating the manual positioning of a posterior resection guide, such as posterior resection guide 300. Robotic system 115 can know the precise location of robotic arm 120, and the geometry and dimensions of partial knee resection guide 400 can be registered to robotic system 115 and computing system 140. As such, the location of posterior resection guide 430, and the dimensions and locations of features therein, in the surgical space can be determined as robotic arm 120 moves posterior resection guide 430 within the surgical space. Robotic arm 120 can therefore align posterior resection guide 430 to set posterior resection guide 430 for a desired flexion gap. In order to eliminate interference with undesirably contacting femur F, posterior resection guide 430 does not include a flange like flange 306 (FIG. 3A). Thus, posterior resection guide 430 can be positioned along a distal resected femur surface at any position to control the gap height between the proximal resected tibia surface and the posterior resected femur surface, based on a surgical plan or surgeon determination without being bound by the thickness of a flanges, such as flange 306. Robotic arm 120 can hold posterior resection guide 430 in place while resections to femur F are made. In an example, robotic arm 120 can position posterior resection guide 430 to align with target axis 340 that is intraoperatively planned with robotic system 115. Pins can be placed through posterior resection guide 430, such as at bore 448, and into femur F to stabilize posterior resection guide 430 in-place at a desired location to perform the posterior resection.

Figure 5B:
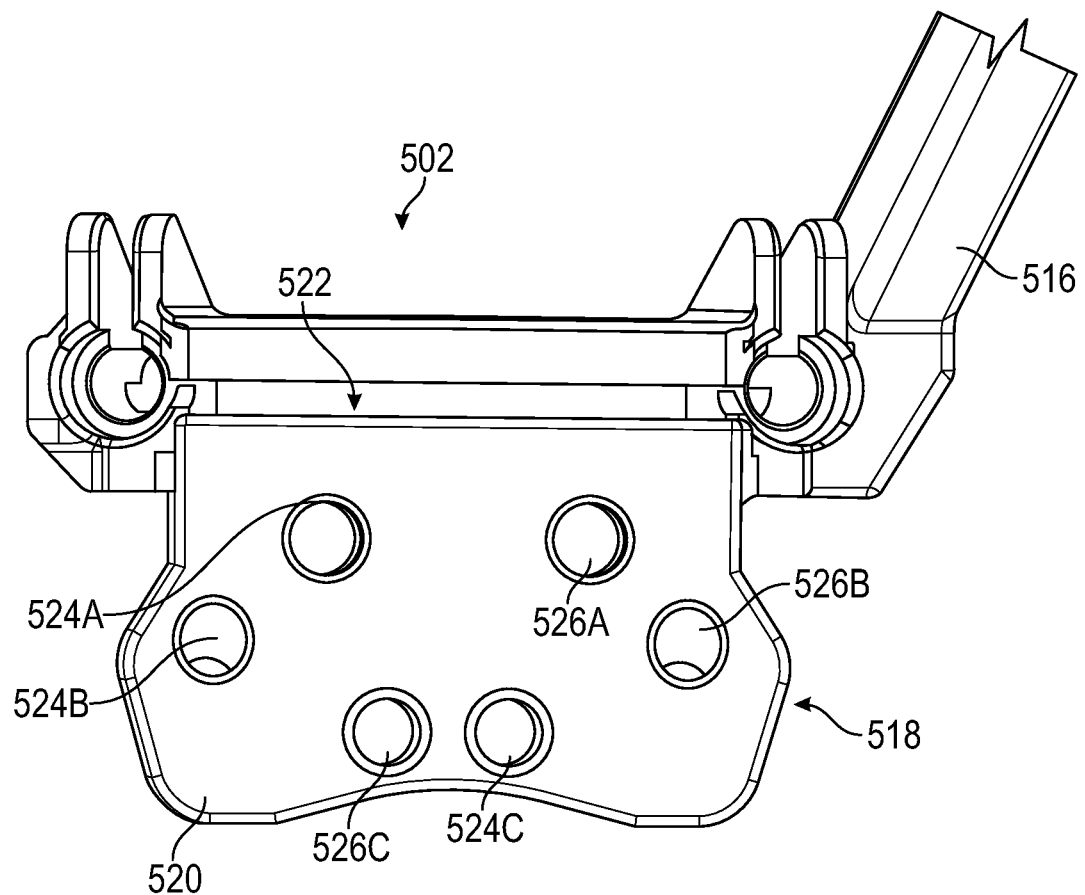
FIG. 5B is a front view of a resection block for a robotically-guided resection instrument configured to couple to the robot-configured posterior cut guide of FIG. 5A.

FIG. 5A is a front view of robot-configured posterior resection guide 500 showing a coupling portion for connecting to a robotically-guided resection instrument. FIG. 5B is a front view of a resection block for robotically-guided partial knee resection guide 502 configured to couple to robot-configured posterior resection guide 500 of FIG. 5A.

Posterior resection guide 500 can comprise body 503 and mounting flange 504. Posterior resection guide 500 can be configured similarly as posterior resection guide 300 of FIGS. 3A and 3B except for the omission of flange 306. Posterior resection guide 500 can be configured similarly as posterior resection guide 430 of FIGS. 4C and 4D except for the inclusion of mounting flange 504 instead of attachment portion 432 and the addition of bores 514A and 514C.

Body 503 can be configured for coupling to partial knee resection guide 502, such as by including mounting flange 504 or other features configured to interact with partial knee resection guide 502. Body 503 can additionally include features for guiding cutting instruments or other instruments against femur F. For example, body 503 can include posterior cut guide surface 508, chamfer cut guide surface 508, anterior peg guide hole 510, posterior peg guide hole 512 and bores 514A, 514B and 514C.

Partial knee resection guide 502 can comprise extension arm 516, which can connect to a tool base similar to tool base 402 of FIG. 4B, and adapter block 518, which can comprise a resection block for resecting the distal portion of femur F, the proximal portion of tibia T and for mounting or aligning posterior resection guide 500.

Adapter block 518 can comprise body 520, guide surface 522, bores 524A, 524B and 524C, and bores 526A, 526B and 526C. Bores 524A-524C and bores 526A-526C can be configured to align with bores 514A-514C, respectively. That is, bores 524A-524C can align with bores 514A-514C when posterior resection guide 500 is positioned on one side of body 520 and bores 526A-526C can align with bores 514A-514C when posterior resection guide 500 is positioned on one side of body 520.

In examples, fasteners can be used to couple posterior resection guide 500 to adapter block 518 at bores 514A-514C, bores 524A-524C and bores 526A-526C. In other examples, adapter block 518 can be moved into position relative to a distal resected femur surface and pin holes can be drilled through bores 524A-524C or bores 526A-526C, adapter block 518, can be moved away from the distal resected femur, pins can be placed into the pin holes, and posterior resection guide 500 can be coupled to the pins using bores 514A-514C such that posterior resection guide 500 can be used to perform the resections of femur F. Such a procedure, e.g., the use of placed pins with resection guide 502, has the benefit of not having to move partial knee resection guide 502 away from femur F to couple to posterior resection guide 500, and then be moved back into place. Furthermore, such a procedure eliminates tolerance staking of the placement of resection guide 502 relative to femur F plus the placement of posterior resection guide 500 relative to resection guide 502.

Figure 6:
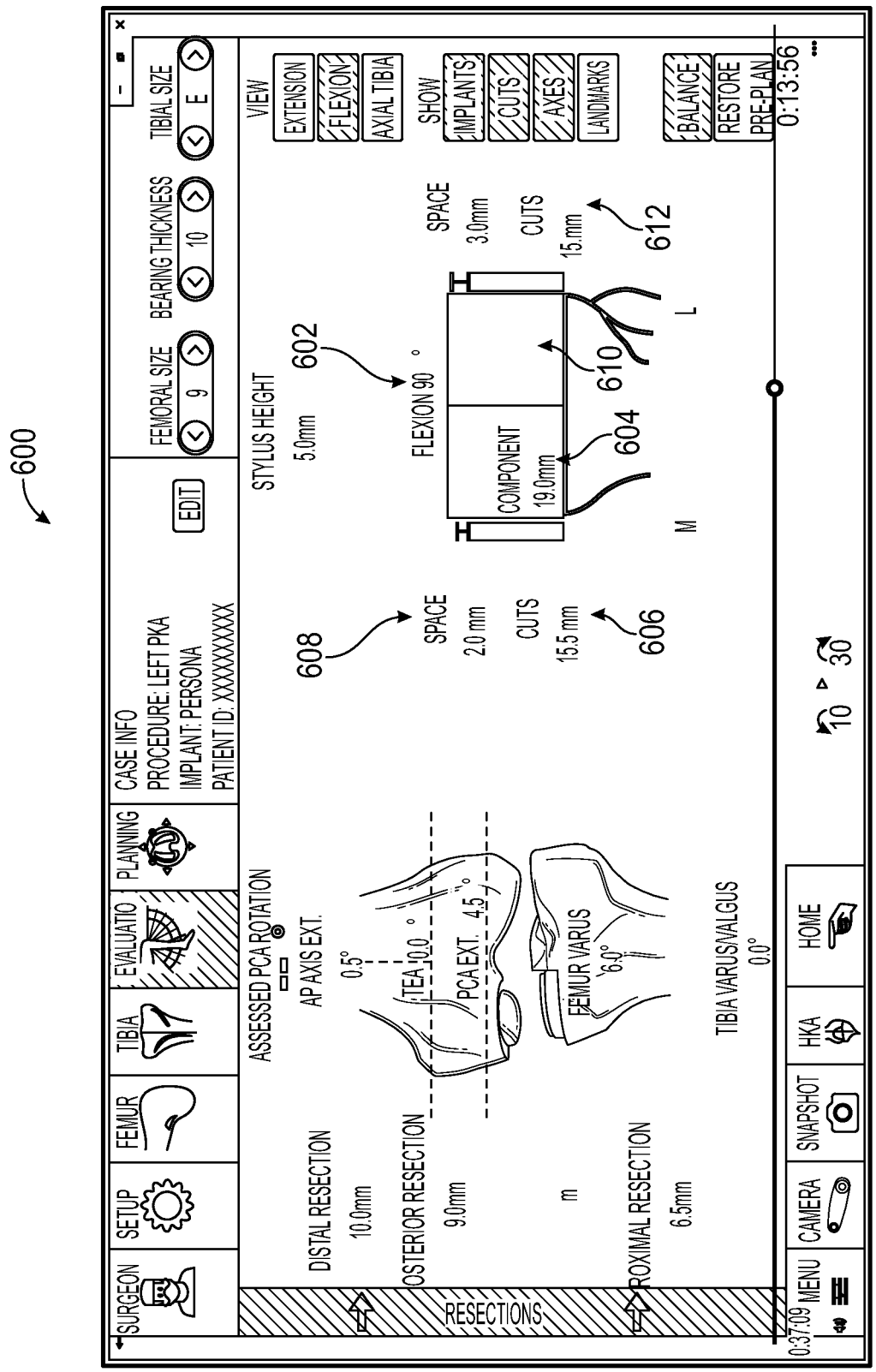
FIG. 6 is a schematic illustration of a surgical planning user inter-face for determining and configuring extension and flexion gap resections for a partial knee arthroplasty.

FIG. 6 is a schematic illustration of surgical planning user interface 600 for determining and configuring a flexion gap resection for a partial knee arthroplasty. User interface 600 can include input 602 for selecting a position of a knee joint, such as extension or flexion. The flexion position can be used to determine the posterior resection of the femur. Input 604 can be used to select a total thickness of a knee implant, including the thicknesses of the femoral component, tibial component and a spacer for positioning therebetween, all for a uni-condylar or partial knee system. Input 606 can be used to select a total thickness of bone to be removed from the joint. Output 608 can indicate an amount of space remaining in the joint, taking into account the amount of bone removed, the thickness of the implant, and laxity in the joint. Input 610 can be used to select a total thickness of a natural knee. Alternatively, input 610 can be used to select a total thickness of an implant, total or partial, for comparison. Thus, input 612 can be used to select as in input or view as an output hypothetical thickness of bone to be removed and an amount of space remaining. In examples, input 610 and input 612 can be fixed to the natural knee joint or can be eliminated from the interface. As such, inputs 602-612 are discussed with reference to the medial side of the knee joint being considered and planned for replacement. However, inputs 602-612 can additionally be used for considering and planning the lateral side of the knee joint for replacement. Thus, user interface 600 can include components for separately planning a partial knee arthroplasty on a lateral side or a medial side of the joint, or a total knee arthroplasty. Input 602 can be changed to indicate a position of the knee for extension such that the amount of bone to be removed from the distal end of the femur can be planned. Thus, using user interface 600 to determine how much of the distal end of the bone is to be removed and how much of the posterior side of the bone is to be removed, a surgeon can obtain an indication of how much laxity will be in the joint after the knee implant is implanted. The surgeon can then vary the amount of the distal resection and posterior resection to obtain desirable laxity and the surgeon can see how varying one parameter affects other parameters to thereby plan a properly placed and fit prosthetic device. The surgeon can select any of the inputs or outputs to be fixed, such as posterior cut, distal cut, any of the device thicknesses, etc., while adjusting other settings to see how one selection affects the others. User interface 600 can be used in conjunction with any of the procedures described herein to pre-operatively plan a surgical procedure that can be used to direct the procedure and intraoperatively adapt the procedure, such as by using the method described with reference to FIG. 3D.

FIG. 7 illustrates system 700 for performing techniques described herein, in accordance with some embodiments. System 700 is an example of a system that can incorporate surgical system 100 of FIG. 1. System 700 can include robotic surgical device 702 (e.g., robotic system 115) coupled to resection guide instrument 704 (e.g., resection guide instrument 200 of FIG. 2), which may interact with tracking system 706. In other examples, the resection guide instruments described herein can be used without tracking system 706. Tracking system 706 can include tracking element 708, camera 710 and registration device 711 (e.g., pointer 326). Resection guide instrument 704 (e.g., instrument 200) can include attachment instruments 712 (e.g., posterior resection guides 300, 430 and 500). System 700 can include display device 714, which can be used to display user interface 716. System 700 can include control system 718 (e.g., a robotic controller or computing system 140 of FIG. 1), including processor 720 and memory 722. In an example, display device 714 can be coupled to one or more of robotic surgical device 702, tracking system 706, or control system 718. As such, data generated by registration device 711 can be shared with control system 718, tracking system 706 and an operator of system 700 via display device 714. In examples, guide instrument 704 can be operated without input from tracking system 700, after a registration process, such that robotic surgical device 702 can be positioned and tracked by movement of robotic arm 120 within the native coordinate system of robotic arm 120. Once in a desired position, resection guide instruments 704 and attachment instruments 712 can be freely used by a surgeon without tracking system 706 required to reacquire position information for robotic surgical device and without control system 718 losing track of the location of robotic surgical device 702.

Figure 8:
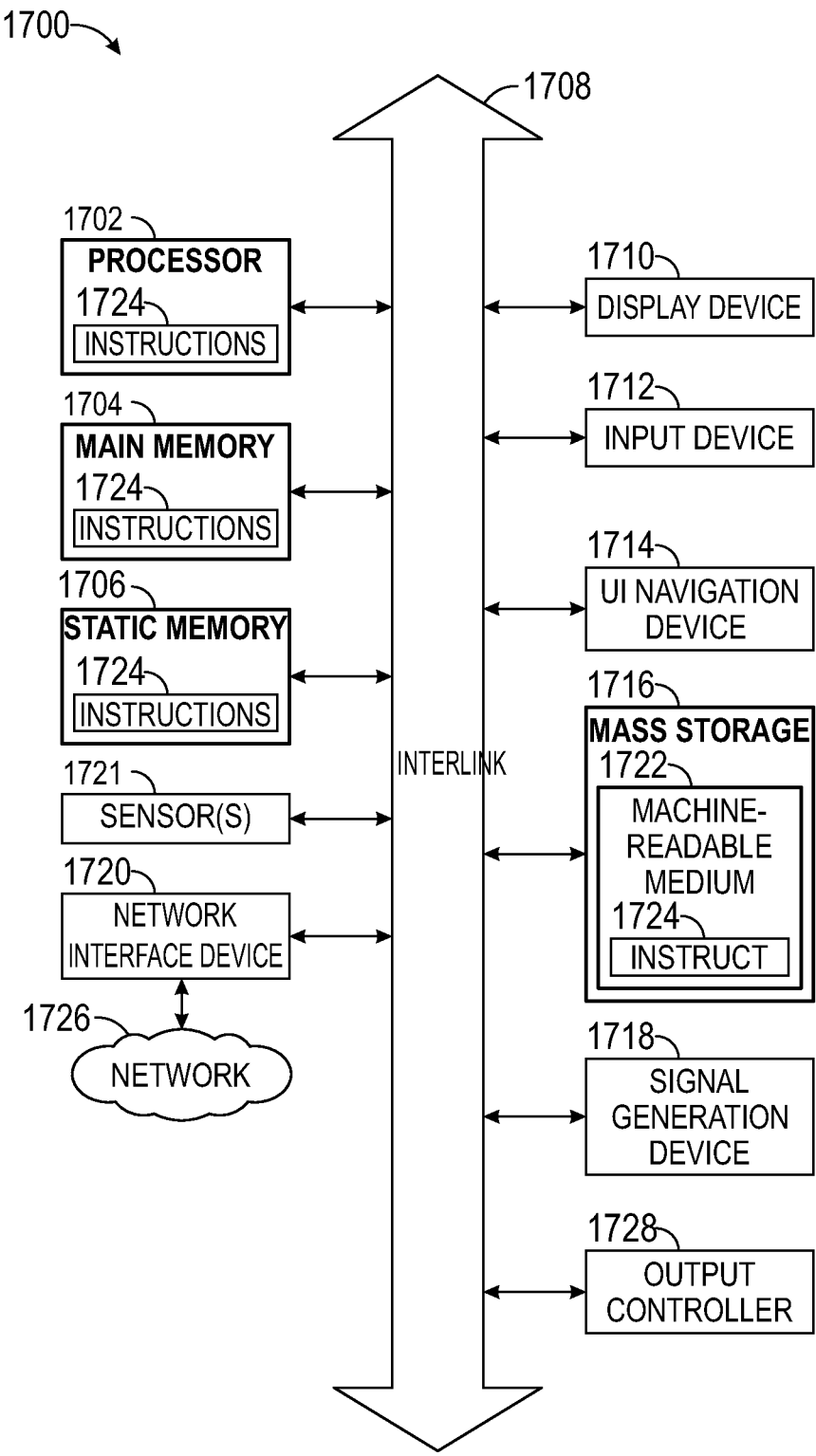
FIG. 8 is a block diagram of an example machine upon which any one or more of the techniques discussed herein may be performed and with which any of the devices discussed herein may be used in accordance with some embodiments.

FIG. 8 illustrates a block diagram of an example machine 1700 upon which any one or more of the techniques discussed herein may be performed in accordance with some embodiments. For example, machine 1700 can comprise computing system 140 of FIG. 1. Machine 1700 can comprise an example of a controller for robotic system 115 and sensors 1721 can include tracking element 170 and tracking device 332. As such instructions 1724 can be executed by processor 1702 to generate and correlate position and orientation information to determine the position and orientation of a surgical instrument relative to robotic arm 120. For example, position and geometric information of partial knee resection guide 400 and partial knee resection guide 502 via a connection to robotic arm 120 relating to the location of resection block 406 and adapter block 518 relative to extension arm 404 and extension arm 516 can be stored in main memory 1704 or static memory 1706 and accessed by processor 1702. Additionally, the shapes and geometric information, such as thicknesses, for gap checker 802, gap checker 860, posterior resection guide 300, posterior resection guide 430 of FIG. 4D and posterior resection guide 500 of FIG. 5A can be stored in memory 1704 and accessed by processor 1702. Processor 1702 can also receive input (such as at input device 1712) relating to the position of tibia T and pointer 326 relative to robotic arm 120 via tracking element 170 and tracking device 332, which can be stored in main memory 1704. Processor 1702 can further relate position information of posterior resection guide 430 and posterior resection guide 500 to the position information of robotic arm 120 through partial knee resection guide 400 and partial knee resection guide 502 to correlate the position of resection block 406 and adapter block 518 to the coordinate system of surgical system 100, such as by being programmed with the shapes, geometries and dimensions thereof. As such, as resection block 406 and adapter block 518, and posterior resection guide 430 and posterior resection guide 500, when attached thereto, moves, machine 1700 can continuously track and update the location of said components relative to robotic arm 120 via movement of robotic arm 120 and, for example, display said position on display unit 1710 (e.g., human interface devices 145), as well as the location of features included thereon, such as cutting guide features.

In alternative embodiments, machine 1700 may operate as a standalone device or may be connected (e.g., networked) to other machines. In a networked deployment, machine 1700 may operate in the capacity of a server machine, a client machine, or both in server-client network environments. In an example, machine 1700 may act as a peer machine in peer-to-peer (P2P) (or other distributed) network environment. Machine 1700 may be a personal computer (PC), a tablet PC, a set-top box (STB), a personal digital assistant (PDA), a mobile telephone, a web appliance, a network router, switch or bridge, or any machine capable of executing instructions (sequential or otherwise) that specify actions to be taken by that machine. Further, while only a single machine is illustrated, the term "machine" shall also be taken to include any collection of machines that individually or jointly execute a set (or multiple sets) of instructions to perform any one or more of the methodologies discussed herein, such as cloud computing, software as a service (SaaS), other computer cluster configurations.

Machine (e.g., computer system) 1700 may include hardware processor 1702 (e.g., a central processing unit (CPU), a graphics processing unit (GPU), a hardware processor core, or any combination thereof), main memory 1704 and static memory 1706, some or all of which may communicate with each other via interlink (e.g., bus) 1708. Machine 1700 may further include display unit 1710, alphanumeric input device 1712 (e.g., a keyboard), and user interface (UI) navigation device 1714 (e.g., a mouse). In an example, display unit 1710, input device 1712 and UI navigation device 1714 may be a touch screen display. Machine 1700 may additionally include storage device (e.g., drive unit) 1716, signal generation device 1718 (e.g., a speaker), network interface device 1720, and one or more sensors 1721, such as a global positioning system (GPS) sensor, compass, accelerometer, or other sensor. Machine 1700 may include output controller 1728, such as a serial (e.g., Universal Serial Bus (USB), parallel, or other wired or wireless (e.g., infrared (IR), near field communication (NFC), etc.) connection to communicate or control one or more peripheral devices (e.g., a printer, card reader, etc.).

Storage device 1716 may include machine readable medium 1722 on which is stored one or more sets of data structures or instructions 1724 (e.g., software) embodying or utilized by any one or more of the techniques, operations or functions described herein, such as those utilized to carry out the methods described with reference to FIG. 13 and elsewhere. Instructions 1724 may also reside, completely or at least partially, within main memory 1704, within static memory 1706, or within hardware processor 1702 during execution thereof by machine 1700. In an example, one or any combination of hardware processor 1702, main memory 1704, static memory 1706, or storage device 1716 may constitute machine readable media.

While machine readable medium 1722 is illustrated as a single medium, the term "machine readable medium" may include a single medium or multiple media (e.g., a centralized or distributed database, and/or associated caches and servers) configured to store the one or more instructions 1724. The term "machine readable medium" may include any medium that is capable of storing, encoding, or carrying instructions for execution by machine 1700 and that cause machine 1700 to perform any one or more of the techniques of the present disclosure, or that is capable of storing, encoding or carrying data structures used by or associated with such instructions. Non-limiting machine readable medium examples may include solid-state memories, and optical and magnetic media.

Instructions 1724 may further be transmitted or received over communications network 1726 using a transmission medium via network interface device 1720 utilizing any one of a number of transfer protocols (e.g., frame relay, internet protocol (IP), transmission control protocol (TCP), user datagram protocol (UDP), hypertext transfer protocol (HTTP), etc.). Example communication networks may include a local area network (LAN), a wide area network (WAN), a packet data network (e.g., the Internet), mobile telephone networks (e.g., cellular networks), Plain Old Telephone (POTS) networks, and wireless data networks (e.g., Institute of Electrical and Electronics Engineers (IEEE) 802.11 family of standards known as Wi-Fi®, IEEE 802.16 family of standards known as WiMax®), IEEE 802.15.4 family of standards, peer-to-peer (P2P) networks, among others. In an example, network interface device 1720 may include one or more physical jacks (e.g., Ethernet, coaxial, or phone jacks) or one or more antennas to connect to communications network 1726. In an example, network interface device 1720 may include a plurality of antennas to wirelessly communicate using at least one of single-input multiple-output (SIMO), multiple-input multiple-output (MIMO), or multiple-input single-output (MISO) techniques. The term "transmission medium" shall be taken to include any intangible medium that is capable of storing, encoding or carrying instructions for execution by machine 1700, and includes digital or analog communications signals or other intangible medium to facilitate communication of such software.

The systems, devices and methods discussed in the present application can be useful in performing robotic-assisted surgical procedures that utilize robotic surgical arms that can be used to position devices relative to a patient to perform arthroplasty procedures, such as partial knee arthroplasties. In particular the systems, devices and methods disclosed herein are useful in improving the accuracy with which posterior cuts and other finishing cuts on a femur are performed. The systems, devices and methods disclosed herein can reduce or eliminate the need for reliance on manually positioning of cutting guides by utilizing surgical guidance systems to orient finishing guides either directly with navigation or through positioning with a robotic surgical arm.

Figure 9:
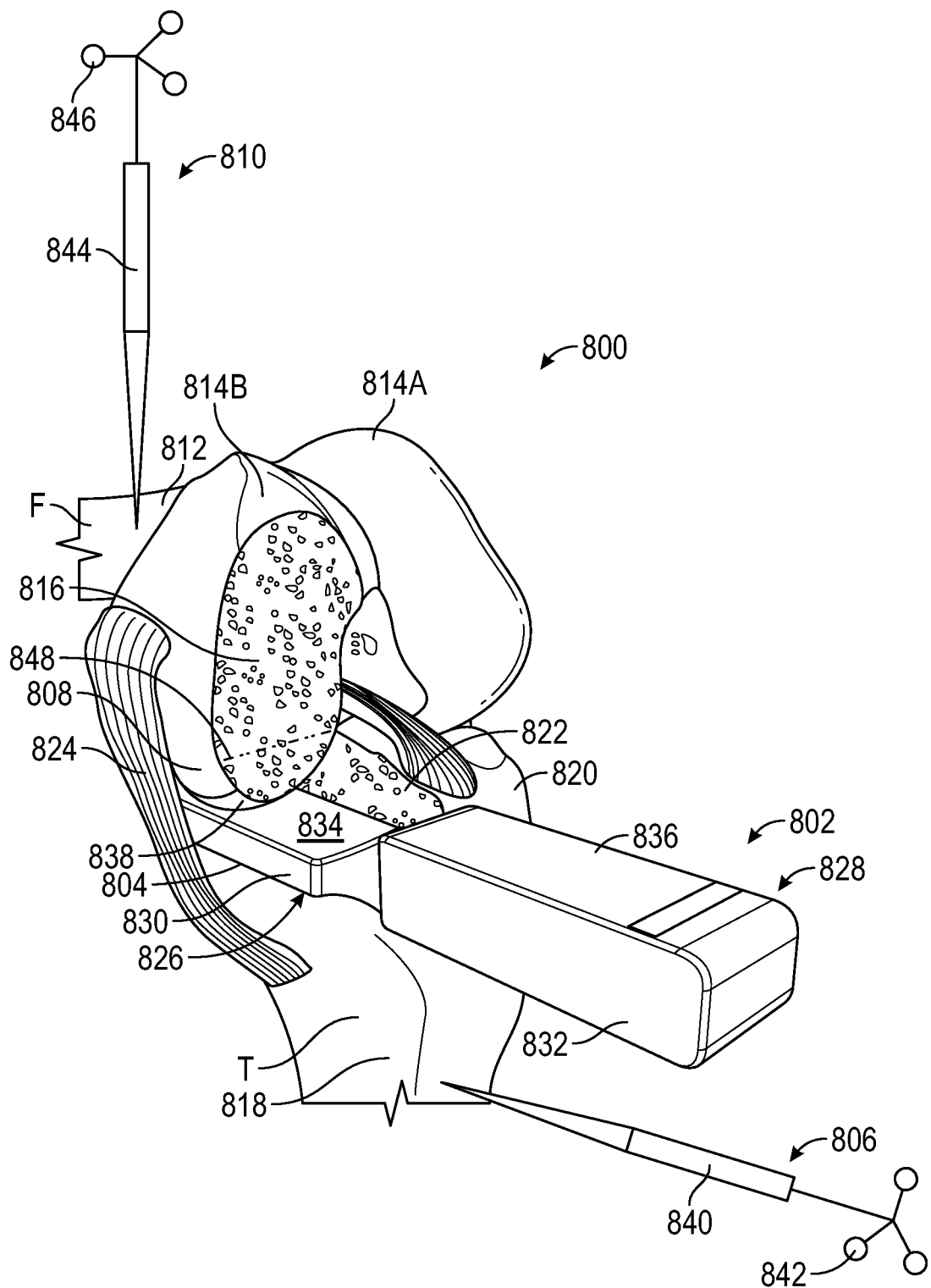
FIG. 9 is a perspective view of a knee joint having a gap checker inserted between a proximal resection of a tibia connected to a first tracker and a posterior portion of a femur connected to a second tracker.

FIG. 9 is a perspective view of a knee joint 800 having gap checker 802 inserted between proximal resection 804 of tibia T connected to first tracker 806 and posterior portion 808 of a femur F connected to second tracker 810. Femur F can include diaphysis region 812 to which second tracker 810 can be attached and epiphysis region including condyles 814A and 814B. The distal portion of condyle 814B can be resected to form resected surface 816. Tibia T can include diaphysis region 818 to which first tracker 806 can be attached and epiphysis region 820 including resected tibial plateau 822. Resected tibial plateau 822 can be resected to form proximal a vertical surface adjacent to proximal resection 804 and opposite condyle 814B. First tracker 806 and second tracker 810 can be configured similarly to pointer 326 pointer tracker device 332 (FIG. 3B). For example, first tracker 806 can comprise pointer 840 and tracker device 842 and second tracker 810 can comprise pointer 844 and tracker device 846.

When knee joint 800 is positioned in extension, proximal resection 804 can face resected surface 816. In order for femur F to receive a uni-condylar implant, posterior portion 808 of condyle 814B is typically resected. As discussed herein, the thickness of the resection of posterior portion 808 of condyle 814B can be determined by placing knee joint 800 in flexion where proximal resection 804 faces posterior portion 808. The amount of bone matter to be removed can be determined based on, for example, surgeon skill and experience in determining joint tension or laxity, such as controlled by tension or laxity in medial collateral ligament (MCL) 824 and other ligaments. To facilitate determination of how much of a resection to take off of posterior portion 808, gap checker 802 can be inserted between proximal resection 804 and posterior portion 808. In this orientation, feature 826 can represent the thickness of the planned tibial component thickness, or possibly represent a simple measurement of the flexion gap. Gap checker 802 can comprise one or more blocks, or gap gauges, having opposing surfaces configured to engage proximal resection 804 and posterior portion 808 of condyle 814B. In examples, the opposing surfaces can be parallel. In the illustrated example, gap checker 802 comprises block 826 and block 828. Block 826 can have sidewall 830 and block 828 can have sidewall 832. Sidewall 830 can have a first thickness between opposing parallel surfaces and sidewall 832 can have a second thickness between opposing parallel surfaces. In particular, block 826 can include upper surface 834 and block 828 can include upper surface 836. Sidewall 832 can be thicker than sidewall 830, as illustrated in FIG. 9. Upper surface 834 and upper surface 836 can provide offset from proximal resection 804 that can be used to set or determine the position for posterior resection guide 430 of FIGS. 4C and 4D and posterior resection guide 500 of FIG. 5A. Additionally, upper surface 834 and upper surface 836 can comprise reference features for the positioning of a cut guide, e.g., posterior resection guide 430 of FIGS. 4C and 4D and posterior resection guide 500 of FIG. 5A, as discussed below.

A surgeon can manually position femur F relative to tibia T to determine a gap height between proximal resection 804 and posterior-most point 838 for performing a posterior resection of condyle 814B. The gap height can be digitized using pointer 840 and pointer 844. Pointer 840 can be engaged with tibia T, such as by pushing a pointed tip into cortical bone matter. Pointer 844 can be engaged with femur F, such as by pushing a pointed tip into cortical bone matter. Thus, tracker device 842 and tracker device 846 can be used to track the locations on the bones where pointers 840 and 844 are engaged. For example, pointers 840 and 844 can be inserted into landmarks, such as boney features, determined from three-dimensional digital models of tibia T and femur F, in order to calibrate the location of tibia T and femur F with the three-dimensional space of surgical area 105. Tracker devices 842 and 846 can be used to send or otherwise communicate real-time positional information to computing system 140 (FIG. 1). Block 826 or block 828 of gap checker 802 can be inserted into the gap between proximal resection 804 and posterior portion 808 of condyle 814B. Once the proper positioning of femur F and tibia T and a gap checker 802 having a desired thickness to set the desired tension of knee joint 800 or MCL 824, the surgeon or a surgical technician can record the positions of femur F and tibia T using computing system 140 (FIG. 1). The location of posterior-most point 838 on condyle 814B and proximal resection 804 can be known to computing system 140 due to, for example, inclusion of three-dimensional coordinates for bone models of femur F and tibia T. As such, the gap height between posterior-most point 838 and proximal resection 804 produced by block 826 can be determined by computing system 140 and digitized to prepare three-dimensional coordinates for the placement of a posterior resection guide. Gap checker 802 can be used to hold the position of femur F and tibia T set by the surgeon to facilitate accurate digitization. The shape of gap checker 802 need not be known to computing system 140. However, as explained with reference to FIG. 11, the geometry of gap checker devices can be stored in memory of computing system 140. After digitizing the gap height, computing system 140 can then compute the location for the resection of condyle 814B above proximal resection 804. For example, computing system 140 can calculate the location above posterior-most point 838 where the posterior-most surface of a prosthetic condyle implant would be located in order for the prosthetic condyle implant and prosthetic tibial component to occupy the same amount of space as gap checker 802 and the bone to be removed, e.g., to replicate the same amount of tension in knee joint 800 or MCL 824 as is being produced with gap checker 802. Thus, computing system 140 can calculate the location for virtual cut plane 848 in the three-dimensional space of surgical area 105 relative to tibia T and femur F. Virtual cut plane 848 can comprise a plane parallel to proximal resection 804 that is spaced from a parallel plane that is tangent to posterior-most point 838 an amount equal to the height of block 826 for the example of FIG. 9. In other words, the plane of upper surface 834 can be digitized as a reference for placement of a posterior resection guide. Thus, robotic arm 120 (FIG. 1) can position posterior cut guide surface 434 of posterior resection guide 430 (FIG. 4C) or resection block 506 of posterior resection guide 500 (FIG. 5A) at a location to align a cut guide surface with virtual cut plane 848 to facilitate removal of a posterior portion of condyle 814B using an appropriate cutting instrument guided along posterior cut guide surface 434 or resection block 506. In examples, the plane of upper surface 834 can comprise a plane where a bottom surface of posterior resection guide 430 or posterior resection guide 500 can be positioned to perform the desired resection at virtual cut plane 848. Thus, FIG. 9 illustrates a method for positioning a posterior resection guide in a three-dimensional coordinate system using a robotic arm to perform a partial knee arthroplasty wherein a gap checker can be used to immobilize a knee joint gap height to allow digitization of a resection plane through known coordinates of tibia T and femur F. In additional examples, the digitization of a reference location for the resection plane can be recorded directly from gap checker 802.

Figure 10:
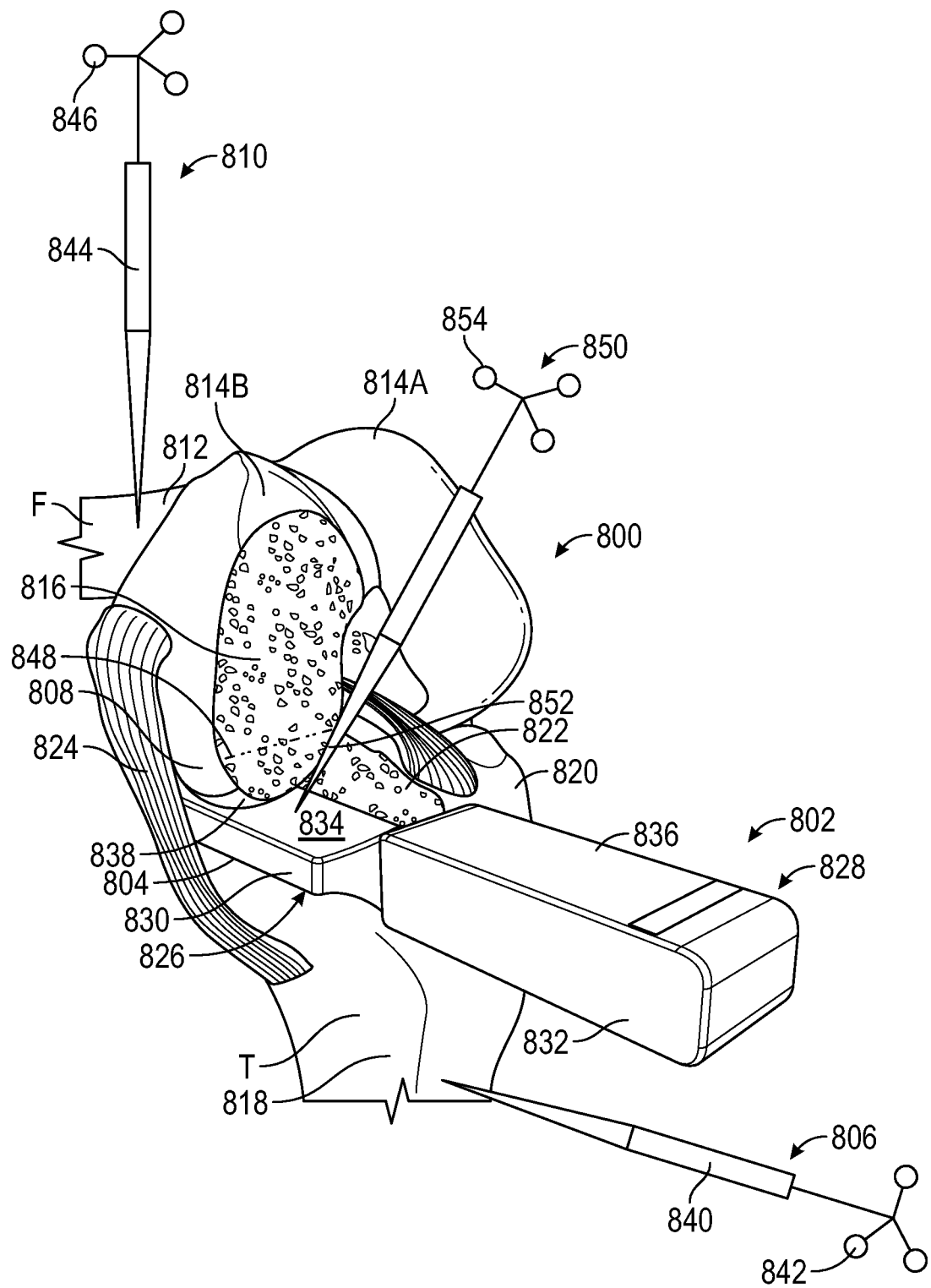
FIG. 10 is a perspective view of a knee joint having a gap checker inserted between a proximal resection of a tibia and a posterior portion of a femur and a tracking device engaged with a proximal surface of the gap checker.

FIG. 10 is a perspective view of knee joint 800 having gap checker 802 inserted between proximal resection 804 of tibia T and posterior portion 808 of femur F and third tracker 850 engaged with upper surface 834 of gap checker 802. Third tracker 850 can comprise pointer 852 and tracker device 854. Third tracker 850 can be used to collect digital points on gap checker 802 for instructing computing system 140 where to position posterior resection guide 430 of FIGS. 4C and 4D and posterior resection guide 500 of FIG. 5A. Upper surface 834 and upper surface 836 can comprise reference features for the positioning of a cut guide, e.g., posterior resection guide 430 of FIGS. 4C and 4D and posterior resection guide 500 of FIG. 5A. In examples, upper surfaces 834 and 836 can comprise reference features for the engagement of bottom surfaces of posterior resection guides 430 and 500.

The configuration of FIG. 10 can be used to determine the location for virtual cut plane 848. Input from third tracker 850 can be used to supplement or fine tune information collected from first tracker 806 and second tracker 810 to determine the location of virtual cut plane 848. Alternatively, input from third tracker 850 can be used as an alternative to information collected from first tracker 806 and second tracker 810 to determine the location of virtual cut plane 848. Thus, in examples, first tracker 806 and second tracker 810 can be omitted from determining the location for virtual cut plane 848, but can be connected to tibia T and femur F for other purposes in performing a partial knee arthroplasty.

As illustrated in FIG. 10, third tracker 850 can be used to digitally mark the location of upper surface 834. Tip of pointer 852 can be touched to upper surface 834, such as by being drawn across or tapped on upper surface 834, to collect multiple points that can be connected by computing system 140 to form a plane. The plane of collected points can be a plane where a bottom surface of posterior resection guide 430 or posterior resection guide 500 can be positioned to perform the desired resection at virtual cut plane 848. Computing system 140 (FIG. 1) can calculate the location of virtual cut plane 848 from upper surface 834 as explained above. Thus, third tracker 850 can be used to directly determine the location of upper surface 834 rather than having to calculate the equivalent location of upper surface 834 through the coordinates of the digital models of tibia T and femur F as can be done using first tracker 806 and second tracker 810 only.

In additional examples, third tracker 850 can be used to mark locations on resected surface 816 directly that can be used as landmarks for the positioning of posterior resection guides 430 and 500. For example, third tracker 850 can be used to directly draw or mark virtual cut plane 848 on resected surface 816.

Thus, FIG. 10 illustrates a method for positioning a posterior resection guide in a three-dimensional coordinate system using a robotic arm to perform a partial knee arthroplasty wherein a gap checker can be used to immobilize a knee joint gap height to allow digitization of a resection plane through coordinates from a surface of the gap checker.

Figure 11:
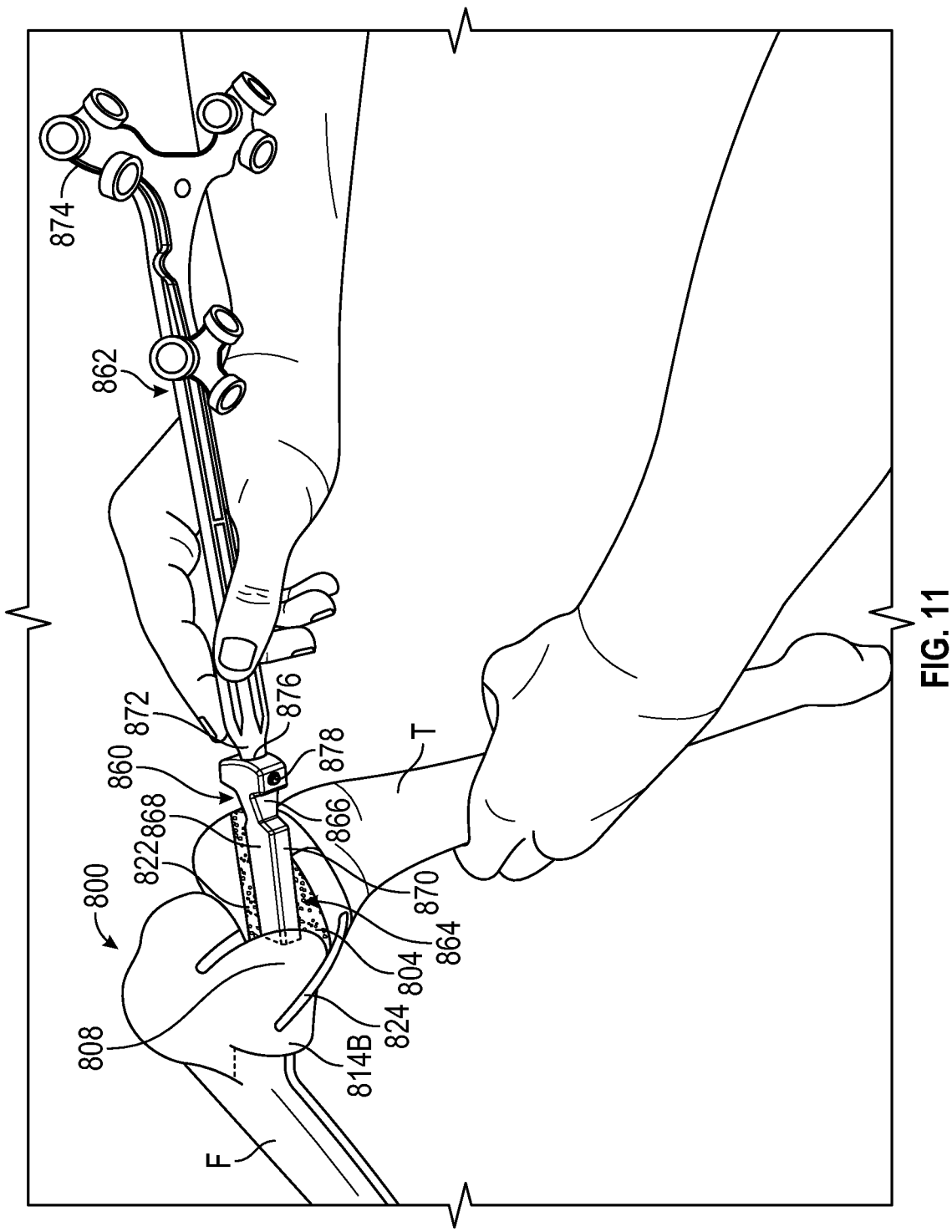
FIG. 11 is a perspective view of a knee joint having a gap checker inserted between a proximal resection of a tibia and a posterior portion of a femur and a tracking device connected to the gap checker.

FIG. 11 is a perspective view of knee joint 800 having gap checker 860 inserted between proximal resection 804 of tibia T and posterior portion 808 of femur F and tracking device 862 connected to gap checker 860. In examples, gap checker 860 can be configured similarly to devices described in Pub. No. US 2022/0183701 to Gogarty et al., the contents of which are hereby incorporated herein by this reference. Gap checker 860 can comprise block 864 and coupler 866. Block 864 can comprise upper surface 868 and sidewall 870. Gap checker 860 can be connected to tracking device 862, which can comprise pointer 872 and tracker device 874. In particular, pointer 872 can be inserted into socket 876 within coupler 866 and fastened thereto via set screw 878. Pointer 872 can include an orientation mechanism (e.g., detent, keying surface) to ensure that pointer 872 and block 864 are attached in a reliable and precise configuration. In examples, pointer 872 can include a threaded aperture at socket 876 and pointer 872 can include a threaded tip. As such, the relative location between tracker device 874 and block 864 can be fixed in a known relationship that can be stored in memory 1704 of computing system 140. Block 864 can be configured similarly to block 826 or block 828 of gap checker 802 of FIGS. 9 and 10. In examples, a plurality of gap checker 860 can be provided and used by a surgeon during a partial knee arthroplasty, with each instance of gap checker 860 having a different thickness of block 864. As such, a surgeon can insert different sized gap checkers 860 between femur F and tibia T until the desired tension in MCL 824 is obtained. The shapes of the various thicknesses of gap checker 860 can be stored in memory of computing system 140. The location of the shape of gap checker 860 can be determined using tracker device 874, including the location of upper surface 868. The plane of upper surface 868 can be a plane where a bottom surface of posterior resection guide 430 or posterior resection guide 500 can be positioned to perform the desired resection at virtual cut plane 848. Computing system 140 (FIG. 1) can calculate the location of virtual cut plane 848 from upper surface 868 as explained above. Thus, tracker device 874 can be used to directly determine the location of upper surface 868 without having to manually collect digital points along upper surface 868 using a separate handheld tracker device.

Thus, FIG. 11 illustrates a method for positioning a posterior resection guide in a three-dimensional coordinate system using a robotic arm to perform a partial knee arthroplasty wherein a gap checker can be used to immobilize a knee joint gap height to allow digitization of a resection plane through coordinates from a surface of the gap checker.

Figure 12:
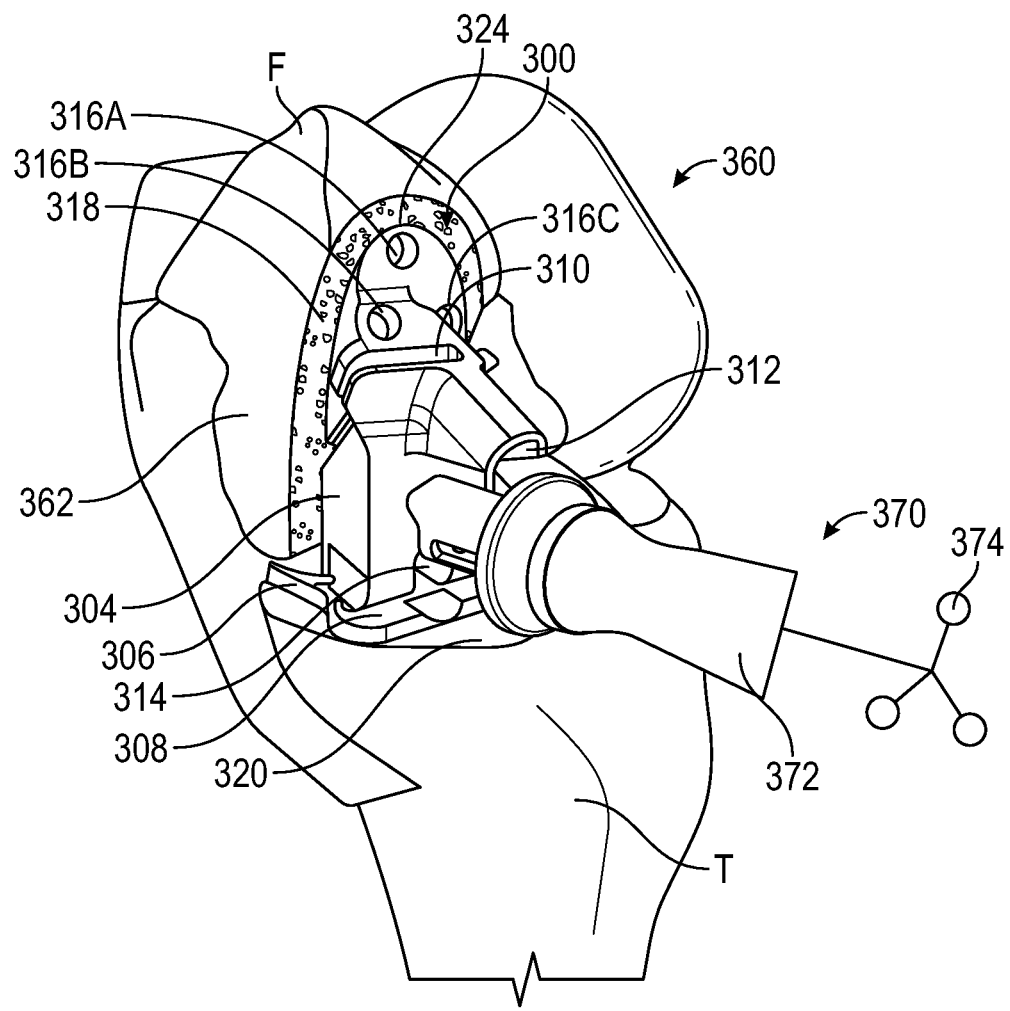
FIG. 12 is a perspective view of a knee joint having a manually-positioned posterior resection guide inserted between a proximal resection of a tibia and a posterior portion of a femur.

FIG. 12 is a perspective view of a knee joint 360 having manually-positioned posterior resection guide 300 inserted between proximal resected surface 320 of tibia T and posterior portion 362 of femur F. Posterior resection guide 300 can be configured as described with reference to FIGS. 3A and 3B. However, rather than posterior resection guide 300 being connected to handle 302 (FIG. 3A), posterior resection guide 300 can be connected to tracker device 370. Tracker device 370 can comprise coupler 372 and tracker element 374. Posterior resection guide 300 can be placed against resected surface 318 such that flange 306 enters the gap between posterior portion 362 and proximal resected surface 320. A surgeon can move the position of posterior resection guide 300 against resected surface 318 to achieve the desired gap height. As discussed above, shims can be positioned above or below flange 306 to facilitate positioning and holding of posterior resection guide 300 in position. As discussed above, tracker device 370 can be used to track the position of posterior resection guide 300 in real-time on a display screen of computing system 140 to move tip 324 to the location of point 350 (FIG. 3D) on the display screen to position posterior resection guide 300 is a desired location. Tracker device 370 can be used to digitize a location for posterior resection guide 300 to determine a location for placement of posterior resection guide 430, which can have the same functional shape as posterior resection guide 300 except for flange 306 and the coupling to tracker device 370 or resection block 406.

Figure 13:
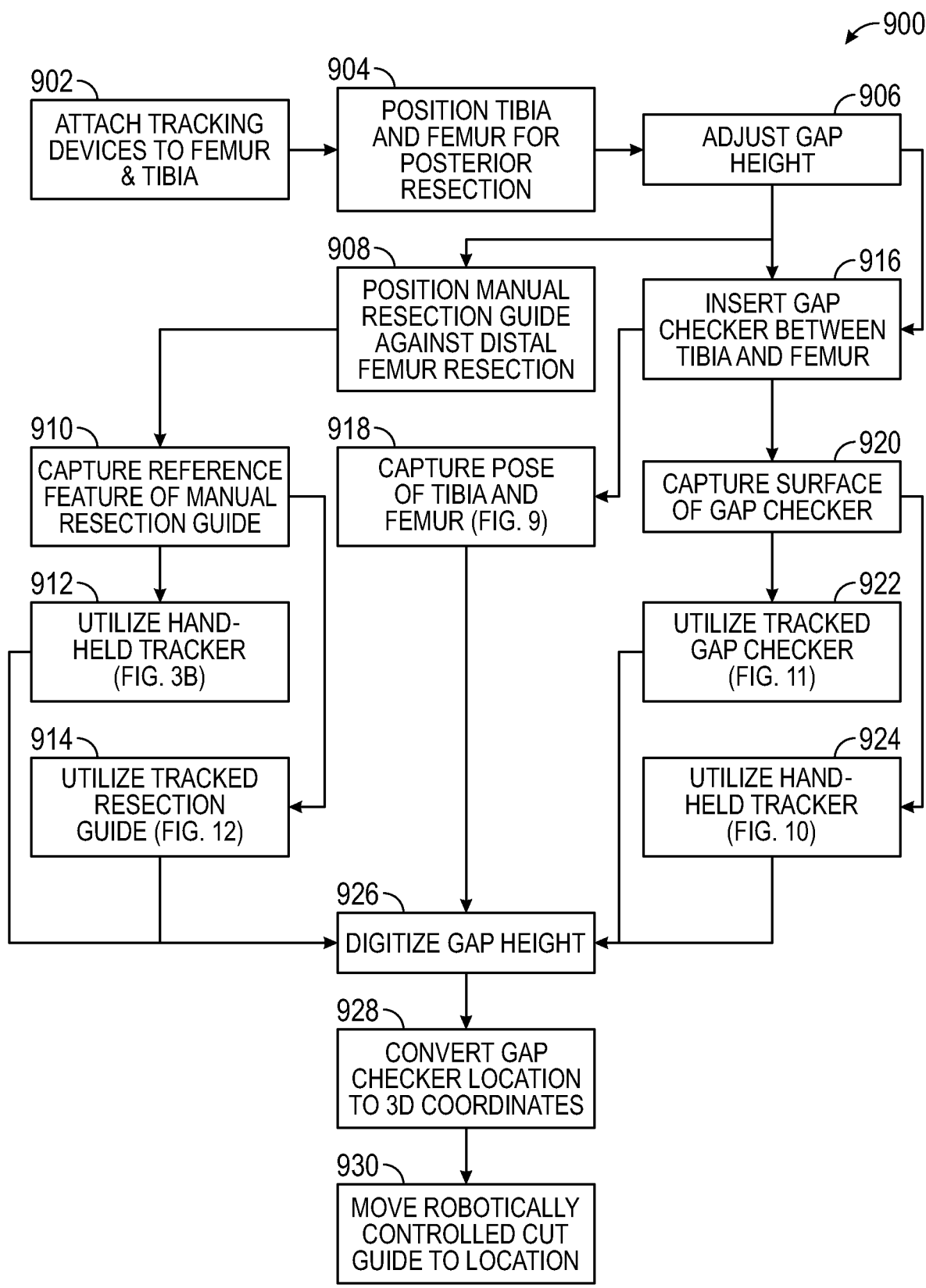
FIG. 13 is a block diagram of examples of methods for obtaining coordinates for and positioning a robotically-controlled posterior resection guide for a partial knee arthroplasty.

FIG. 13 is a block diagram of examples of methods 900 for obtaining coordinates for and positioning a posterior resection guide for a partial knee arthroplasty. Method 900 can comprise operation 902 through operation 930 that describe various procedures for performing a partial posterior resection of a femur. In various examples, additional operations consistent with the systems, methods and operations described herein can be included, and some of operation 902 through operation 930 can be omitted. Furthermore, operation 902—operation 930 can be performed in different orders than the illustrated example.

At operation 902, tracking devices can be attached to tibia T and femur F. For example, first tracker 806 can be attached to tibia T and second tracker 810 can be attached to femur F.

At operation 904, tibia T and femur F can be positioned relative to each other for performing a posterior resection of femur F. For example, knee joint 800 can be put into flexion after proximal resection 804 of tibia T has been performed. As such, the gap between condyle 814B and proximal resection 804 can be accessed by a surgeon.

At operation 906, the gap height between posterior-most point 838 and proximal resection 804 can be adjusted. For example, a surgeon can adjust the gap height to provide knee joint 800 with desirable laxity, e.g., laxity that reproduces the feel of a natural knee joint. A surgeon can rely on experience and intraoperative observation of knee joint 800 to determine the desired laxity. In examples, the surgeon can set the laxity, e.g., gap height, of knee joint 800 free-hand without the use of other instruments or gap checkers. In examples, a surgeon can utilize one or both of posterior resection guide 300 and a gap checker, such as gap checker 802 of FIGS. 9 and 10 or gap checker 860 of FIG. 11, to adjust the gap height.

At operation 908, a surgeon can position posterior resection guide 300 in relationship to femur F. For example, body 304 can be positioned against resected surface 816 and flange 306 can be positioned in the gap. In examples, posterior resection guide 300 can be positioned on top of other devices, such as shims 342 (FIG. 3D) or gap checker 802 (FIG. 9), to adjust the gap height. In examples, flange 306, shims and gap checkers can be used to hold the gap height at a fixed distance to allow for digitization.

At operation 910, a reference feature of posterior resection guide 300 can be digitized. That is, a surgeon can position posterior resection guide 300 against distal resected surface 816 in a location where the posterior cut is to be performed. The digitized reference feature can be subsequently converted into three-dimensional coordinate information in surgical area 105 for robotic arm 120 to position posterior resection guide 430 of FIG. 4D or posterior resection guide 500 of FIG. 5A.

At operation 912, pointer 326 of FIGS. 3B and 3C can be engaged with posterior resection guide 300. Pointer 326 can be traced along a feature of posterior resection guide 300. In examples, pointer 326 can be traced along tip 324 of the anterior flange, as discussed with reference to FIG. 3B. In examples, pointer 326 can trace along cut guide surface 308.

At operation 914, tracker device 370 can be coupled to posterior resection guide 300, such as is shown in FIG. 12. Tracker device 370 can be attached to posterior resection guide 300 in a fixed manner such that the entire geometry or just specific reference features of posterior resection guide 300, such as tip 324 or cut guide surface 308, can be known to computing system 140.

As an alternative to operations 908-914, some or all of operations 916-924 can be performed.

At operation 916, a gap checker can be inserted into the space between posterior-most point 838 and proximal resection 804. For example, gap checker 802 of FIGS. 9 and 10 can be used or gap checker 860 of FIG. 11 can be used. The gap checkers can be used to hold the gap height at a fixed distance to allow for digitization.

At operation 918, gap checker 802 can be inserted between posterior-most point 838 and proximal resection 804. Blocks 826 and 828 can be inserted therein to test the laxity of knee joint 800 for different thicknesses. After a surgeon has positioned a block of a gap checker having the desired thickness into the gap, the pose of tibia T and femur F can be captured using tracker device 842 and tracker device 846. As described herein, tracker devices 842 and 846 can be used to determine the position between tibia T and femur F including the gap height between posterior-most point 838 and proximal resection 804. Computing system 140 can utilize the recorded gap height produced by the gap checker inserted in the gap to determine a location for posterior resection guide 430 of FIG. 4D or posterior resection guide 500 of FIG. 5A to perform a posterior resection that will reproduce the set gap height after prosthetic components are implanted.

At operation 920, a feature of a gap checker can be digitized or recorded to provide a reference location for computing system 140 to position posterior resection guide 430 of FIG. 4D or posterior resection guide 500 of FIG. 5A.

At operation 922, tracked gap checker 860 of FIG. 11 can be used. The entire geometry of tracked gap checker 860 can be known to computing system 140 due to the correlation of gap checker 860 and tracking device 862.

At operation 924, gap checker 802 of FIG. 10 can be used in conjunction with third tracker 850. Third tracker 850 can be used to record specific features of gap checker 802 for digitization by computing system 140.

At operation 926, the reference positions and features captured at operations 910-924 can be digitized for computing system 140 and robotic system 115. As discussed herein, the digitized surfaces and features can be used to record a location in the 3D space of surgical area 105 for the placement of posterior resection guide 430 of FIG. 4D or posterior resection guide 500 of FIG. 5A relative to tibia T and femur F with robotic arm 120.

At operation 928, the captured reference positions and features of operation 926 can be converted to instructions for the positioning of posterior resection guide 430 of FIG. 4D or posterior resection guide 500 of FIG. 5A. Computing system 140 can convert the digitized reference position or features to the desired position of cut guide surface 434 or resection block 506 by extrapolating the location of cut guide surface 434 or resection block 506 from the geometry of instruments they are attached to, such as resection guide 400 and resection guide 500.

At operation 929, a surgeon can perform final checks and adjustment of the positioning of the femur and tibia relative to each other. Digitizing aspects of gap checker 802, such as upper surface 834, and features of resection guide 300, such as anterior tip 324, as described with reference to FIGS. 9-12 are important for determining and freezing or locking the relative tibial-femoral orientation in a three-dimensional coordinate system. Such orientation can result when the MCL is appropriately tensed to reflect the final implanted state. The surgeon can additionally fine-tune other aspects of the placement of the femoral cut guide per direct observation and surgeon preference. For example, the surgeon can adjust the size of the femoral implant, the interior-exterior rotation of the cut guide, the medial-lateral position of the cut guide, as well as other parameters. In examples, such surgeon-implemented adjustments do not adjust the positioning between the femur and tibia determined in the preceding steps or operations, but can provide adjustment of the femoral bone cut plane within the gap envelope determined by the position between the femur and tibia. Such surgeon-implemented adjustments can be used to address component peripheral fit on the cut, appropriate rotation to the patella, ability to centralize the ninety-degree contact part of the femur over the center of the tibia, as well as other parameters.

At operation 930, robotic arm 120 can move posterior resection guide 430 of FIG. 4D or posterior resection guide 500 of FIG. 5A to the instructed location against femur F to perform the posterior resection. Robotic arm 120 can move posterior resection guide 430 of FIG. 4D or posterior resection guide 500 of FIG. 5A to the desired location without a surgeon having to hold a manual cut guide in place. A surgeon can guide a cutting blade of a cutting instrument against or along posterior cut guide surface 434 or resection block 506.

EXAMPLES

Example 1 can include or use subject matter such as a method for aligning a posterior resection guide with a distal femur surface that can comprise positioning a posterior resection guide adjacent a proximal resected surface of a tibia and a posterior surface of a femur for a knee joint in flexion, displaying a representation of a distal end of the femur on graphical display, displaying an alignment axis on the representation, engaging a tracking device to the posterior resection guide, tracking an anterior tip of the posterior resection guide on a graphical display, and rotating the posterior resection guide to align the anterior tip with the alignment axis on the graphical display.

Example 2 can include, or can optionally be combined with the subject matter of Example 1, to optionally include an performing a posterior resection of the femur using a guide surface on the posterior resection guide.

Example 3 can include, or can optionally be combined with the subject matter of one or any combination of Examples 1 or 2 to optionally include generating the alignment axis by aligning a center of a tibia plateau with a femoral condyle with the knee joint in extension, marking the distal end of the femur with a distal indicator, rotating the knee joint into flexion to project the center of the tibia plateau onto a posterior side of the femoral condyle, marking a posterior surface of the femur with a posterior indicator, and projecting an axis from the posterior indicator, through the distal indicator to a location on an anterior side of the femur.

Example 4 can include, or can optionally be combined with the subject matter of one or any combination of Examples 1 through 3 to optionally include a engaging the tracking device to the posterior resection guide by attaching the tracking device to an instrument, and engaging a geometric feature of the instrument with the anterior tip of the posterior resection guide.

Example 5 can include, or can optionally be combined with the subject matter of one or any combination of Examples 1 through 4 to optionally include engaging the tracking device to the posterior resection guide by mounting the tracking device to the posterior resection guide.

Example 6 can include, or can optionally be combined with the subject matter of one or any combination of Examples 1 through 5 to optionally include positioning the posterior resection guide adjacent the proximal resected surface of the tibia and the posterior surface of the femur by inserting a flange projecting from the posterior resection guide between the proximal resected surface and the posterior surface such that the posterior resection guide engages the distal femur surface.

Example 7 can include, or can optionally be combined with the subject matter of one or any combination of Examples 1 through 6 to optionally include a posterior resection guide that is manually positioned adjacent the distal femur surface and a posterior resection guide that is manually rotated to align the anterior tip with the alignment axis on the graphical display.

Example 8 can include or use subject matter such as a system for performing femoral resections for a partial knee arthroplasty that can comprise a surgical robot comprising an articulating arm configured to move within a coordinate system for the surgical robot, a femoral resection guide instrument comprising a coupler for connecting to the articulating arm, an extension arm extending from the coupler, and a resection block attached to the extension arm, and a finishing guide for performing a posterior resection of a distal femur, wherein the finishing guide is positionable by the surgical robot to determine a thickness and rotation of the posterior cut.

Example 9 can include, or can optionally be combined with the subject matter of Example 8, to optionally include a resection block that can comprise a cutting guide surface, and a plurality of pin bores.

Example 10 can include, or can optionally be combined with the subject matter of one or any combination of Examples 8 or 9 to optionally include a finishing guide that is positionable by the surgical robot via placement of pin holes with the resection block.

Example 11 can include, or can optionally be combined with the subject matter of one or any combination of Examples 8 through 10 to optionally include a finishing guide that can include a flange having a plurality of bores arranged in a pattern that align with a pattern of the plurality of bores of the resection block.

Example 12 can include, or can optionally be combined with the subject matter of one or any combination of Examples 8 through 11 to optionally include a finishing guide that is positionable by the surgical robot via engagement with the resection block.

Example 13 can include, or can optionally be combined with the subject matter of one or any combination of Examples 8 through 12 to optionally include a finishing guide that can comprise a coupling flange configured to engage a slot formed by the cutting guide surface or one or more bores of the plurality of pin bores.

Example 14 can include, or can optionally be combined with the subject matter of one or any combination of Examples 8 through 13 to optionally include a controller for the surgical robot that can comprise a non-transitory storage medium having computer-readable instructions stored therein comprising dimensional data for the femoral resection guide instrument, dimensional data for the finishing guide, and instructions for moving an end of the articulating arm to position the finishing guide into specific locations within the coordinate system according to a surgical plan.

Example 15 can include or use subject matter such as a method for resecting a distal femur for a partial knee arthroplasty that can comprise attaching a resection guide instrument to an articulating arm of a robotic surgical system, moving the resection guide instrument to an anterior or posterior side of a distal end of a femur, resecting the distal end of the femur to form a distal resection surface, moving the resection guide instrument to the distal resection surface, drilling holes into the distal resection surface through the guide bores in the resection guide instrument, inserting pins into the drilled holes, attaching a finishing guide to the inserted pins, and resecting a posterior side of the femur adjacent the distal resection surface using the finishing guide to guide a cutting instrument.

Example 16 can include, or can optionally be combined with the subject matter of Example 15, to optionally include moving the resection guide instrument to a proximal end of a tibial, and resecting the proximal end of the tibia to form a proximal resection surface.

Example 17 can include, or can optionally be combined with the subject matter of one or any combination of Examples 15 or 16 to optionally include resecting a chamfer cut on the femur adjacent the distal resection surface and the resected posterior side of the femur using a chamfer guide surface of the finishing guide.

Example 18 can include or use subject matter such as a method for aligning a posterior resection guide with a distal resected femur surface that can comprise positioning a posterior resection guide adjacent the distal resected femur surface, inserting a flange of the posterior resection guide between a posterior surface of a femur and a proximal resected surface of a tibia, moving the posterior resection guide medial-laterally to observe a rim thickness between an anterior edge of the posterior resection guide relative to an edge of the distal resected femur surface, and positioning shims adjacent the flange to vary the rim thickness.

Example 19 can include or use subject matter such as a system for performing femoral resections for a partial knee arthroplasty that can comprise a surgical robot comprising an articulating arm configured to move within a coordinate system for the surgical robot, a tracking system configured determine locations of one or more trackers in the coordinate system, a tracker configured to be tracked by the tracking system, a finishing guide configured to be coupled to the articulating arm to perform a posterior resection of a distal femur, a controller for the surgical robot that can comprise a communication device configured to receive data from and transmit data to the surgical robot and the tracking system, a display device for outputting visual information from the surgical robot and the tracking system, and a non-transitory storage medium having computer-readable instructions stored therein comprising marking digital locations at a distal end and a posterior surface of a distal end of a femur using the tracker, displaying the digital locations of the distal end and posterior surface on the display device, plotting a target axis extending through the distal end and the posterior surface on the display device, projecting the target axis to an anterior surface of the femur, and moving the articulating arm to align the finishing guide along the target axis at the anterior surface.

Example 20 can include, or can optionally be combined with the subject matter of Example 19, to optionally include a femoral resection guide instrument that can comprise a coupler for connecting to the articulating arm, an extension arm extending from the coupler, and a resection block attached to the extension arm.

Example 21 can include, or can optionally be combined with the subject matter of one or any combination of Examples 19 or 20 to optionally include a finishing guide that can be coupled to the resection block so that the articulating arm can position the finishing guide along the target axis.

Example 22 can include, or can optionally be combined with the subject matter of one or any combination of Examples 19 through 21 to optionally include a resection guide that can further comprise a first plurality of pin holes and a finishing guide that can further comprise a second plurality of pin holes, wherein the articulating arm can position the first plurality of pin holes so that bores can be drilled to receive pins that receive the second plurality of pin bores.

Example 23 can include, or can optionally be combined with the subject matter of one or any combination of Examples 19 through 22 to optionally include a non-transitory storage medium that has computer-readable instructions stored therein further comprising dimensional data for the femoral resection guide instrument, dimensional data for the finishing guide, and instructions for moving an end of the articulating arm to position the finishing guide into specific locations within the coordinate system according to a surgical plan.

Example 24 is a method of positioning a posterior resection guide in a three-dimensional coordinate system using a robotic arm in order to perform a partial knee arthroplasty, the method comprising: connecting a first tracking device for a surgical tracking system of the robotic arm to a femur; connecting a second tracking device for the surgical tracking system of the robotic arm to a tibia; manually positioning the tibia relative to the femur to a desired orientation to perform a posterior resection; manually determining a position for the posterior resection guide to perform the posterior resection; digitizing a reference point for the posterior resection guide in the three-dimensional coordinate system for a location of a feature of the posterior resection guide; moving the posterior resection guide to the location in the three-dimensional coordinate system with the robotic arm; and resecting a posterior portion of a condyle of the femur using the posterior resection guide to guide a cutting instrument.

In Example 25, the subject matter of Example 24 optionally includes wherein the reference point for the posterior resection guide in the three-dimensional coordinate system for the location of the posterior resection guide comprises a digital reference location for the feature of the posterior resection guide on a distal end of the femur.

In Example 26, the subject matter of Example 25 optionally includes wherein the feature comprises an anterior tip of the posterior resection guide.

In Example 27, the subject matter of Example 26 optionally includes wherein marking the digital reference location comprises engaging a tracked-pointer device with a location on an anterior side of the condyle to be resected.

In Example 28, the subject matter of Example 27 optionally includes wherein engaging the tracked-pointer device with the location on the anterior side of the condyle to be resected comprises: marking a first location at a distal location of the condyle in extension; and marking a second location at a posterior location on the condyle in flexion; and drawing a line through the first and second locations to the location on the anterior side of the condyle.

In Example 29, the subject matter of any one or more of Examples 26-28 optionally include wherein marking the digital reference location comprises engaging a third tracking device with an analogous feature of a manually positioned posterior resection guide for the feature.

In Example 30, the subject matter of any one or more of Examples 26-29 optionally include wherein marking the digital reference location comprises utilizing a third tracking device coupled to a manually positioned posterior resection guide.

In Example 31, the subject matter of any one or more of Examples 26-30 optionally include wherein marking the digital reference location comprises marking a location of a resection guide surface on a manually positioned posterior resection guide.

In Example 32, the subject matter of any one or more of Examples 25-31 optionally include resecting a distal portion of the femur after digitizing the reference point for the posterior resection guide in the three-dimensional coordinate system for the location of the posterior resection guide.

In Example 33, the subject matter of any one or more of Examples 24-32 optionally include wherein the reference point for the posterior resection guide in the three-dimensional coordinate system for the location of the posterior resection guide comprises a digital reference location for the feature of the posterior resection guide relative to a proximal surface of the tibia.

In Example 34, the subject matter of Example 33 optionally includes resecting a proximal portion of the tibia before digitizing the reference point for the posterior resection guide in the three-dimensional coordinate system for the location of the posterior resection guide.

In Example 35, the subject matter of any one or more of Examples 33-34 optionally include wherein the feature comprises a distal surface of the posterior resection guide.

In Example 36, the subject matter of Example 35 optionally includes wherein digitizing the reference point for the posterior resection guide in the three-dimensional coordinate system for the location of the posterior resection guide comprises: digitizing a distance between a proximal resection surface of the tibia and an unresected posterior condyle of the femur.

In Example 37, the subject matter of Example 36 optionally includes wherein manually positioning the tibia to the femur comprises inserting a gap control device between a proximal portion of the tibia and a posterior portion of the femur.

In Example 38, the subject matter of Example 37 optionally includes wherein marking the digital reference location comprises engaging a tracked-pointer device with a proximal surface of the gap control device.

In Example 39, the subject matter of any one or more of Examples 37-38 optionally include wherein marking the digital reference location comprises recording a tracked location of the gap control device using tracking capabilities attached to the gap control device.

In Example 40, the subject matter of any one or more of Examples 37-39 optionally include manually positioning a posterior resection guide on the gap control device.

In Example 41, the subject matter of any one or more of Examples 37-40 optionally include wherein digitizing the distance between a proximal resection surface of the tibia and an unresected posterior condyle of the femur comprises capturing a pose of the femur relative to the tibia with the first tracking device and the second tracking device.

In Example 42, the subject matter of any one or more of Examples 24-41 optionally include converting the digitized reference point to coordinates in the three-dimensional coordinate system for a location of the posterior resection guide; calculating a position of the feature on the posterior resection guide relative to the robotic arm when the posterior resection guide is coupled to the robotic arm; and moving the feature of the posterior resection guide mounted to the robotic arm to the location.

In Example 43, the subject matter of any one or more of Examples 24-42 optionally include holding positioning of the tibia relative to the femur to fix a gap height between the tibia and femur.

In Example 44, the subject matter of Example 43 optionally includes wherein manually determining a position for the posterior resection guide to perform the posterior resection comprises positioning a gap gauge into a gap between a proximal portion of the tibia and a posterior portion of the femur.

In Example 45, the subject matter of Example 44 optionally includes manually positioning the posterior resection guide into engagement with the gap gauge.

In Example 46, the subject matter of Example 45 optionally includes manually positioning the posterior resection guide on the gap gauge, the gap gauge comprising a gap checker block.

In Example 47, the subject matter of any one or more of Examples 45-46 optionally include manually positioning a flange of the posterior resection guide into the gap with the gap gauge, the gap gauge comprising a shim.

Each of these non-limiting examples can stand on its own, or can be combined in various permutations or combinations with one or more of the other examples.

VARIOUS NOTES

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventor also contemplates examples in which only those elements shown or described are provided. Moreover, the present inventor also contemplates examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code may form portions of computer program products. Further, in an example, the code can be tangibly stored on one or more volatile, non-transitory, or non-volatile tangible computer-readable media, such as during execution or at other times. Examples of these tangible computer-readable media can include, but are not limited to, hard disks, removable magnetic disks, removable optical disks (e.g., compact disks and digital video disks), magnetic cassettes, memory cards or sticks, random access memories (RAMs), read only memories (ROMs), and the like.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

The claimed invention is:

1. A method of positioning a posterior resection guide in a three-dimensional coordinate system using a robotic arm in order to perform a partial knee arthroplasty, the method comprising:
   connecting a first tracking device for a surgical tracking system of the robotic arm to a femur;
   connecting a second tracking device for the surgical tracking system of the robotic arm to a tibia;
   manually positioning the tibia relative to the femur to a desired orientation to perform a posterior resection;
   manually determining a position for the posterior resection guide to perform the posterior resection;
   digitizing a reference point for the posterior resection guide in the three-dimensional coordinate system for a location of a feature of the posterior resection guide;
   moving the posterior resection guide to the location in the three-dimensional coordinate system with the robotic arm; and
   resecting a posterior portion of a condyle of the femur using the posterior resection guide to guide a cutting instrument.

2. The method of claim 1, wherein digitizing the reference point for the posterior resection guide in the three-dimensional coordinate system for the location of the posterior resection guide comprises marking a digital reference location for the feature of the posterior resection guide on a distal end of the femur.

3. The method of claim 2, wherein the feature comprises an anterior tip of the posterior resection guide.

4. The method of claim 3, wherein marking the digital reference location comprises engaging a tracked-pointer device with a location on an anterior side of the condyle to be resected.

5. The method of claim 4, wherein engaging the tracked-pointer device with the location on the anterior side of the condyle to be resected comprises:
   marking a first location at a distal location of the condyle in extension; and
   marking a second location at a posterior location on the condyle in flexion; and
   drawing a line through the first and second locations to the location on the anterior side of the condyle.

6. The method of claim 3, wherein marking the digital reference location comprises engaging a third tracking device with an analogous feature of a manually positioned posterior resection guide for the feature.

7. The method of claim 3, wherein marking the digital reference location comprises utilizing a third tracking device coupled to a manually positioned posterior resection guide.

8. The method of claim 3, wherein marking the digital reference location comprises marking a location of a resection guide surface on a manually positioned posterior resection guide.

9. The method of claim 2, further comprising resecting a distal portion of the femur after digitizing the reference point for the posterior resection guide in the three-dimensional coordinate system for the location of the posterior resection guide.

10. The method of claim 1, wherein digitizing the reference point for the posterior resection guide in the three-dimensional coordinate system for the location of the posterior resection guide comprises marking a digital reference location for the feature of the posterior resection guide relative to a proximal surface of the tibia.

11. The method of claim 10, further comprising resecting a proximal portion of the tibia before digitizing the reference point for the posterior resection guide in the three-dimensional coordinate system for the location of the posterior resection guide.

12. The method of claim 10, wherein the feature comprises a distal surface of the posterior resection guide.

13. The method of claim 12, wherein digitizing the reference point for the posterior resection guide in the three-dimensional coordinate system for the location of the posterior resection guide comprises:
digitizing a distance between a proximal resection surface of the tibia and an unresected posterior condyle of the femur.

14. The method of claim 13, wherein manually positioning the tibia relative to the femur comprises inserting a gap control device between a proximal portion of the tibia and a posterior portion of the femur.

15. The method of claim 14, wherein marking the digital reference location comprises engaging a tracked-pointer device with a proximal surface of the gap control device.

16. The method of claim 14, wherein marking the digital reference location comprises recording a tracked location of the gap control device using tracking capabilities attached to the gap control device.

17. The method of claim 14, further comprising manually positioning a posterior resection guide on the gap control device.

18. The method of claim 14, wherein digitizing the distance between a proximal resection surface of the tibia and an unresected posterior condyle of the femur comprises capturing a pose of the femur relative to the tibia with the first tracking device and the second tracking device.

19. The method of claim 1, further comprising:
converting the digitized reference point to coordinates in the three-dimensional coordinate system for a location of the posterior resection guide;
calculating a position of the feature on the posterior resection guide relative to the robotic arm when the posterior resection guide is coupled to the robotic arm; and
moving the feature of the posterior resection guide mounted to the robotic arm to the location.

20. The method of claim 1, further comprising holding positioning of the tibia relative to the femur to fix a gap height between the tibia and femur.

21. The method of claim 20, wherein manually determining a position for the posterior resection guide to perform the posterior resection comprises positioning a gap gauge into a gap between a proximal portion of the tibia and a posterior portion of the femur.

22. The method of claim 21, further comprising manually positioning the posterior resection guide into engagement with the gap gauge.

23. The method of claim 22, further comprising manually positioning the posterior resection guide on the gap gauge, the gap gauge comprising a gap checker block.

24. The method of claim 22, further comprising manually positioning a flange of the posterior resection guide into the gap with the gap gauge, the gap gauge comprising a shim.

* * * * *